(12) United States Patent
Hallinan et al.

(10) Patent No.: US 8,637,699 B2
(45) Date of Patent: Jan. 28, 2014

(54) PROCESS FOR THE MANUFACTURE OF ACETIC ACID

(75) Inventors: Noel C. Hallinan, Loveland, OH (US); Brian Salisbury, Oxford, PA (US); Wayne Joseph Brtko, Glen Mills, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 468 days.

(21) Appl. No.: 13/088,145

(22) Filed: Apr. 15, 2011

(65) Prior Publication Data

US 2012/0264971 A1     Oct. 18, 2012

(51) Int. Cl.
*C07C 51/12* (2006.01)

(52) U.S. Cl.
USPC ..................................................... 562/519

(58) Field of Classification Search
None
See application file for complete search history.

(56) References Cited

U.S. PATENT DOCUMENTS

| | | | |
|---|---|---|---|
| 5,416,237 A | 5/1995 | Aubigne et al. | |
| 5,442,107 A * | 8/1995 | Beevor et al. | 562/519 |
| 5,817,869 A | 10/1998 | Hinnenkamp et al. | |
| 6,031,129 A | 2/2000 | Hinnenkamp et al. | |
| 6,307,057 B1 | 10/2001 | MacMillan et al. | |
| 6,552,221 B1 | 4/2003 | Hallinan et al. | |
| 6,916,951 B2 | 7/2005 | Tustin et al. | |
| 7,115,774 B2 | 10/2006 | Magna et al. | |
| 7,582,792 B2 | 9/2009 | Zoeller et al. | |
| 7,629,491 B2 | 12/2009 | Zoeller et al. | |
| 7,737,298 B2 | 6/2010 | Kline et al. | |
| 7,790,919 B2 | 9/2010 | Hallinan et al. | |
| 2003/0212295 A1 | 11/2003 | Charles et al. | |
| 2007/0293695 A1 | 12/2007 | Zoeller et al. | |

FOREIGN PATENT DOCUMENTS

| | | |
|---|---|---|
| EP | 0391680 A1 | 4/1990 |
| EP | 0506240 A2 | 9/1992 |
| EP | 1364936 A1 | 11/2003 |

\* cited by examiner

*Primary Examiner* — Yevegeny Valenrod

(57) ABSTRACT

The disclosure relates to a process in which methanol is carbonylated in a reaction zone in the presence of a catalyst to obtain a reaction mixture (A) comprising acetic acid, hydrogen iodide, methyl iodide, water and the catalyst. At least a part of the reaction mixture (A) is separated in a flash zone to obtain a vapor stream ($B_V$) which comprises acetic acid, hydrogen iodide, methyl iodide and water. The vapor stream ($B_V$) is withdrawn from the flash zone, and the withdrawn vapor stream is then reacted with at least one alkylimidazole to obtain a composition (C) from which acetic acid is separated. By reacting the vapor stream ($B_V$) with the alkylimidazole at least parts of the hydrogen iodide and methyl iodide contained in ($B_V$) are bound in form of iodide salts which significantly facilitates the separation of crude acetic acid from the vapor stream ($B_V$) and the further purification of the crude acetic acid.

14 Claims, 12 Drawing Sheets

Figure 1:

$$CH_3OH + HI \rightleftharpoons CH_3I + H_2O \quad (A)$$

$$[Rh(CO)_2I_2]^- + CH_3I \longrightarrow [CH_3Rh(CO)_2I_3]^- \quad (B)$$

$$[CH_3Rh(CO)_2I_3]^- + CO \longrightarrow [CH_3C(O)Rh(CO)_2I_3]^- \quad (C)$$

$$[CH_3C(O)Rh(CO)_2I_3]^- \longrightarrow CH_3C(O)I + [Rh(CO)_2I_2]^- \quad (D)$$

$$CH_3C(O)I + H_2O \longrightarrow CH_3C(O)OH + HI \quad (E)$$

$$H_2O + CO \rightleftharpoons CO_2 + H_2 \quad (F)$$

$$CH_3C(O)OH + CH_3OH \longrightarrow CH_3C(O)OCH_3 \quad (G)$$

$$CH_3C(O)OCH_3 + HI \longrightarrow CH_3C(O)OH + CH_3I \quad (H)$$

Figure 2 – Prior Art:
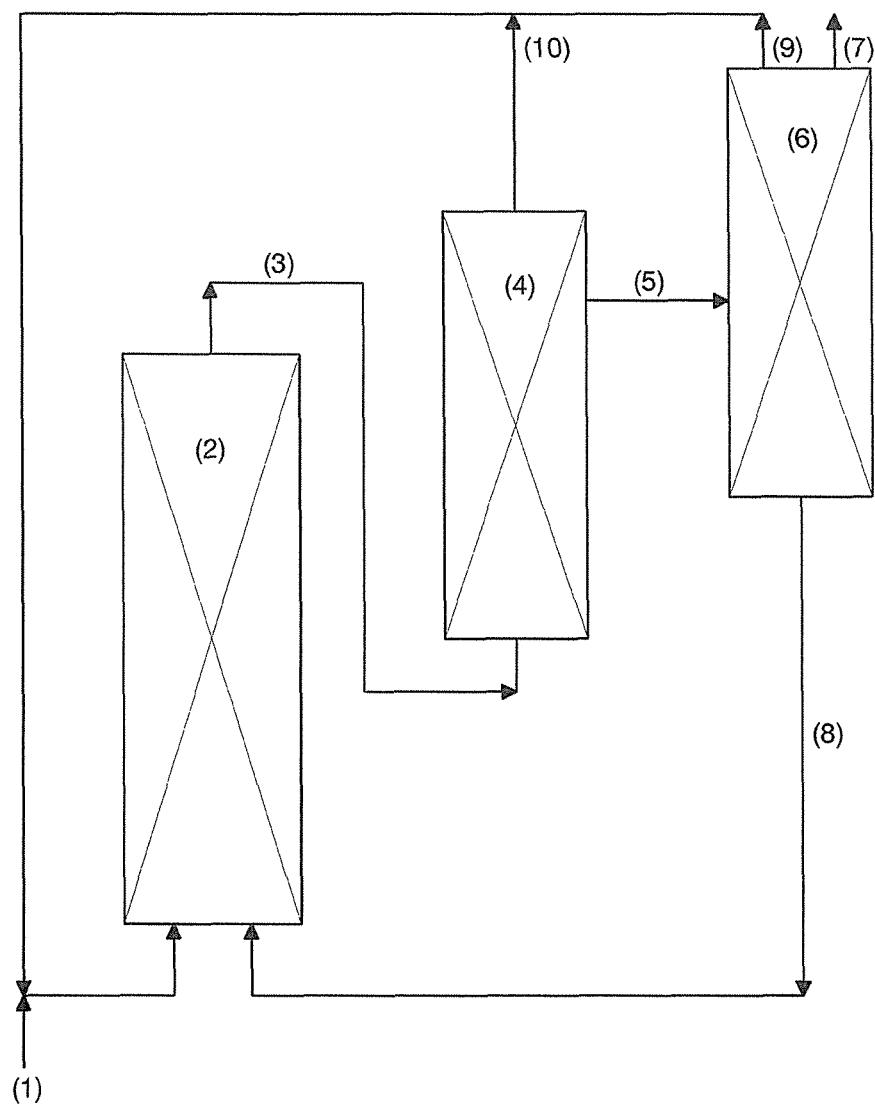

PROCESS FOR THE MANUFACTURE OF ACETIC ACID

FIELD OF THE DISCLOSURE

The disclosure relates to the manufacture of acetic acid. More particularly, the disclosure relates to a process in which methanol is carbonylated in a reaction zone in the presence of a catalyst to obtain a reaction mixture (A) comprising acetic acid, hydrogen iodide, methyl iodide, water and the catalyst. At least a part of the reaction mixture (A) is separated in a flash zone to obtain a vapor stream ($B_V$) which comprises acetic acid, hydrogen iodide, methyl iodide and water. The vapor stream ($B_V$) is withdrawn from the flash zone, and the withdrawn vapor stream is then reacted with at least one alkylimidazole to obtain a composition (C) from which acetic acid is separated.

By reacting the vapor stream ($B_V$) with the alkylimidazole at least parts of the hydrogen iodide and methyl iodide contained in ($B_V$) are bound in form of an iodide salt which significantly facilitates the separation of crude acetic acid from the vapor stream ($B_V$) and the further purification of the crude acetic acid. Hydrogen iodide poses corrosion issues and is involved in the formation of long chain alkyl iodide by-products such as hexyl iodide which are hard to separate from acetic acid. The present process significantly reduces the amounts of hydrogen iodide which may become entrained in the crude acetic acid. On the one hand, the amount is reduced because hydrogen iodide and the alkylimidazole form a high boiling alkylimidazolium iodide salt. On the other hand, high boiling iodide salts formed by reaction of the alkylimidazole with hydrogen iodide and with methyl iodide interact with hydrogen iodide thus further reducing the amount of hydrogen iodide which may be vaporized. The present process, therefore, alleviates corrosion problems as well as problems caused by the formation of undesired by-products.

BACKGROUND OF THE DISCLOSURE

The manufacture of acetic acid by carbonylating methanol in the presence of a catalyst is of major industrial importance as acetic acid is employed in a wide variety of applications. While the reaction per se can be represented by

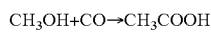

the underlying chemistry is intricate and involves a multiplicity of interrelated reactions, by-products, and equilibria. To be practicable, a manufacturing process, therefore, has to balance those reactions, the associated by-products, and the purification of the product.

Prior to 1970, acetic acid was produced using a cobalt catalyst. A rhodium carbonyl iodide catalyst was developed in 1970 by Monsanto. The rhodium catalyst is considerably more active than the cobalt catalyst, which allows lower reaction pressure and temperature. Most importantly, the rhodium catalyst gives high selectivity to acetic acid.

One of the problems associated with the original Monsanto process is that a large amount of water (about 14% by weight of the reaction mixture) is needed to produce hydrogen in the reactor via the water-gas shift reaction

Water and hydrogen are necessary to react with precipitated Rh(III) and inactive [$Rh_4(CO)_2$] to regenerate the active Rh(I) catalyst. However, a large amount of water increases the formation of hydrogen iodide. Hydrogen iodide is a necessary intermediate in the reactions involved in the formation of acetic acid. However, increased amounts of hydrogen iodide are undesirable because the corrosive nature of hydrogen iodide causes engineering problems. Additionally, hydrogen iodide is involved in the formation of undesired by-products, in particular long chain alkyl iodides such as hexyl iodide, which are hard to separate from the acetic acid product. Further, removing a large amount of water from the acetic acid product renders the process more costly.

In the late '70s Celanese modified the carbonylation process by introducing lithium iodide to the reaction mixture. Lithium iodide increases the catalyst stability by minimizing side reactions which produce inactive Rh(III) species. Consequently, the amount of water which is necessary to stabilize the catalyst can be reduced. Additionally, lithium iodide has been found to decrease the vaporization tendency of water, see, e.g., EP 506 240. The process, thus, has advantages with regard to the separation of water and acetic acid. However, the respective process modification does not alleviate the problems associated with hydrogen iodide.

In the early '90s, Millennium Petrochemicals developed a new rhodium carbonylation catalyst system that does not use a metal iodide as catalyst stabilizer. Instead, the catalyst system employs a pentavalent Group 15 oxide such as triphenylphosphine oxide as a catalyst stabilizer. The Millennium catalyst system not only reduces the amount of water needed but also increases the carbonylation rate and acetic acid yield, see, e.g., U.S. Pat. Nos. 5,817,869 and 6,031,129.

Further attempts to ensure stabilization of the catalyst while reducing the amount of water employed in the carbonylation of methanol involve the use of ionic liquids, i.e., phosphonium or ammonium iodides, which are liquid under the conditions of the carbonylation reaction. The ionic liquids are proposed as catalyst stabilizer, i.e., EP 391 680, U.S. Pat. Nos. 5,416,237, and 7,115,774, or as solvent, i.e., U.S. Pat. Nos. 6,916,951, 7,115,774. While the ionic liquids are described to be advantageous in as much as they allow a further reduction of the water content, these processes have the disadvantage that ionic liquids are expensive and the processes employing them, thus, are uneconomical and not competitive.

In general, acetic acid is produced in a plant which can be conveniently divided into three functional areas, i.e., the reaction, the light ends recovery, and the purification. In general, the reaction area comprises a reactor or reaction zone and a flash tank or flash zone. The light ends recovery area comprises a light ends distillation column or fractioning zone and a phase separation vessel, e.g., a decanter. The light ends distillation column may also be part of the purification area, which in turn further comprises a drying column and optionally a heavy ends distillation column.

The primary purpose of the flash tank or flash zone is to separate the catalyst from the crude reaction mixture. The light ends distillation column or fractioning zone is critical to the process as it serves two purposes, namely, (i) to purify crude acetic acid, and (ii) to recover hydrogen iodide which otherwise may be lost from the process. Ideally, hydrogen iodide is recovered with the bottom stream formed in the fractioning zone. The bottom stream usually comprises acetic acid, water and hydrogen iodide. Hydrogen iodide forms a high boiling azeotrope in acetic acid solutions having greater than about 5 wt. % water. If the water concentration in the bottom stream falls below about 5 wt. %, azeotropic breakdown and hydrogen iodide volatilization occurs. Such volatilization leads to less hydrogen iodide in the bottom stream returning to the reaction section and, thus, may adversely impact reactor iodide inventory. Also, volatilized hydrogen iodide becomes part of the aqueous acetic acid stream which is withdrawn from the fractioning zone for further purification. Process equipment generally used in the manufacture of acetic acid is substantially inert to the components. However, the equipment may be corroded or otherwise adversely affected when the amount of hydrogen iodide in the purification section reaches excessively high levels. Additionally, hydrogen iodide gives rise to the formation of long chain alkyl iodide impurities such as, e.g., hexyl iodide, which are hard to remove and which complicate the purification of acetic acid. Thus, the presence of significant amounts of hydrogen iodide in the aqueous acetic acid which is recovered from the fractioning zone has consequences both in terms of corrosion of purification vessels and in terms of hydrogen iodide and alkyl iodide contamination of the final acetic acid product.

Accordingly, there continues to be a need to further improve the carbonylation of methanol to produce acetic acid. In particular, there continues to be a need to reduce or to eliminate entertainment of hydrogen iodide in the crude acetic acid which is recovered from the fractioning zone.

SUMMARY OF THE DISCLOSURE

In a first aspect, the present disclosure relates to a process for producing acetic acid wherein the process comprises:
(a) carbonylating methanol in the presence of a catalyst in a reaction zone to obtain a reaction mixture (A) comprising acetic acid, hydrogen iodide, methyl iodide, water and the catalyst;
(b) separating at least a part of the reaction mixture (A) in a flash zone to obtain a liquid stream ($B_L$) comprising the catalyst, and a vapor stream ($B_V$) comprising acetic acid, hydrogen iodide, methyl iodide and water, and withdrawing the vapor stream ($B_V$) from the flash zone;
(c) reacting the withdrawn vapor stream ($B_V$) with at least one alkylimidazole to obtain a composition (C); and
(d) separating the acetic acid from the composition (C).

In a second aspect, the present disclosure provides for a process in accordance with the foregoing aspect in which step (d) further comprises:
($d_1$) fractioning the composition (C) in a fractioning zone to obtain a product stream ($D_P$) comprising the acetic acid and a liquid stream ($D_L$) comprising water and at least one iodide salt formed by reacting the alkylimidazole with hydrogen iodide or with methyl iodide.

In a third aspect, the present disclosure provides for a process in accordance with the second aspect wherein the vapor stream ($B_V$) and the at least one alkylimidazole are reacted in the fractioning zone.

In a forth aspect, the present disclosure provides for a process in accordance with the second or third aspect wherein the liquid stream ($D_L$) is recycled to the reaction zone.

In a fifth aspect, the present disclosure provides for a process in accordance with the second, third or fourth aspect wherein the liquid stream ($D_L$) is recycled to the reaction zone by firstly introducing ($D_L$) into the flash zone to obtain a combination of the liquid streams ($D_L$) and ($B_L$), and subsequently recycling at least a part of the combination of ($D_L$) and ($B_L$) to the reaction zone.

In a sixth aspect, the present disclosure provides for a process in accordance with the fourth or fifth aspect wherein the at least one alkylimidazole is employed in step (c) in an amount sufficient to establish a steady state concentration of from about 2 to about 20% by weight of the iodide salt in the reaction mixture (A).

In a seventh aspect, the present disclosure provides for a process in accordance with any one of the foregoing aspects wherein the alkylimidazole is a compound of formula (I)

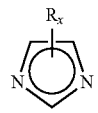

wherein x is 1, 2 or 3, and each R independently is $C_1$-$C_6$-alkyl.

In an eighth aspect, the present disclosure provides for a process in accordance with any one of the foregoing aspects wherein the alkylimidazole is a compound of formula (Ia)

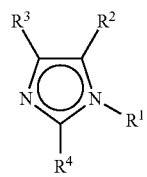

wherein
$R^1$ is hydrogen, or $C_1$-$C_6$-alkyl;
$R^2$, $R^3$, $R^4$ each independently, is hydrogen, or $C_1$-$C_2$-alkyl; and wherein at least one of $R^1$, $R^2$, $R^3$ and $R^4$ is different from hydrogen, and at least one of $R^1$, $R^2$, $R^3$ and $R^4$ is hydrogen.

In a ninth aspect, the present disclosure provides for a process in accordance with any one of the foregoing aspects wherein the alkylimidazole is 1-methylimidazole, 1-ethylimidazole, 1-propylimidazole, 1-isopropylimidazole, 1-(1-butyl)imidazole, 1-(2-butyl)imidazole, 1-isobutylimidazole, 1-tert-butylimidazole, 3-methylimidazole, 3-ethylimidazole, 4-methylimidazole, 4-ethylimidazole, 1,4-dimethylimidazole, 1,4-diethylimidazole, 1-ethyl-4-methylimidazole, 4-ethyl-1-methylimidazole, 2-methyl-1-propylimidazole, 4-methyl-1-propylimidazole, 5-methyl-1-propylimidazole, 2,4-dimethyl-1-propylimidazole, 2,5-dimethyl-1-propylimidazole, 1-isopropyl-2-methylimidazole, 1-isopropyl-4-methylimidazole, 1-isopropyl-5-methylimidazole, 2,4-dimethyl-1-isopropylimidazole, 2,5-dimethyl-1-isopropylimidazole, 1-(1-butyl)-2-methylimidazole, 1-(1-butyl)-4-methylimidazole, 1-(1-butyl)-5-methylimidazole, 1-(1-butyl)-2,4-dimethylimidazole, 1-(1-butyl)-2,5-dimethylimidazole, 1-(2-butyl)-2-methylimidazole, 1-(2-butyl)-4-methylimidazole, 1-(2-butyl)-5-methylimidazole, 1-(2-butyl)-2,4-dimethylimidazole, 1-(2-butyl)-2,5-dimethylimidazole, 1-isobutyl-2-methylimidazole, 1-isobutyl-4-methylimidazole, 1-isobutyl-5-methylimidazole, 2,4-dimethyl-1-isobutylimidazole, 2,5-dimethyl-1-isobutylimidazole, 1-tert-butyl-2-methylimidazole, 1-tert-butyl-4-methylimidazole, 1-tert-butyl-5-methylimidazole, 1-tert-butyl-2,4-dimethylimidazole, or 1-tert-butyl-2,5-dimethylimidazole.

In a tenth aspect, the present disclosure provides for a process in accordance with any one of the foregoing aspects wherein the catalyst is a rhodium catalyst.

In an eleventh aspect, the present disclosure provides for a process in accordance with any one of the foregoing aspects wherein the catalyst comprises at least one stabilizer selected from the group consisting of phosphine oxides and iodides of a metal of Group 1 and 2 of the Periodic Table of the Elements.

In a twelfth aspect, the present disclosure provides for a process in accordance with the foregoing eleventh aspect wherein the stabilizer is triphenylphosphine oxide and/or lithium iodide.

In a thirteenth aspect, the present disclosure provides for a process in accordance with any one of the foregoing aspects wherein the catalyst does not comprise a phosphine oxide and/or a iodide of a metal of Group 1 or 2 of the Periodic Table of the Elements.

In a fourteenth aspect, the present disclosure provides for a process in accordance with any one of the foregoing aspects wherein the reaction mixture (A) comprises water in a concentration of from about 2% to about 10% by weight.

BRIEF DESCRIPTION OF THE DRAWINGS

FIG. 1 sets forth some of the interrelated reactions and equilibria believed to be involved in the carbonylation of methanol in the presence of a rhodium catalyst.

FIG. 2 illustrates a diagrammatic flow chart of a prior art process for carbonylating alcohol in a non-aqueous ionic liquid (U.S. Pat. No. 7,115,774).

DETAILED DESCRIPTION OF THE DISCLOSURE

Figure 3:
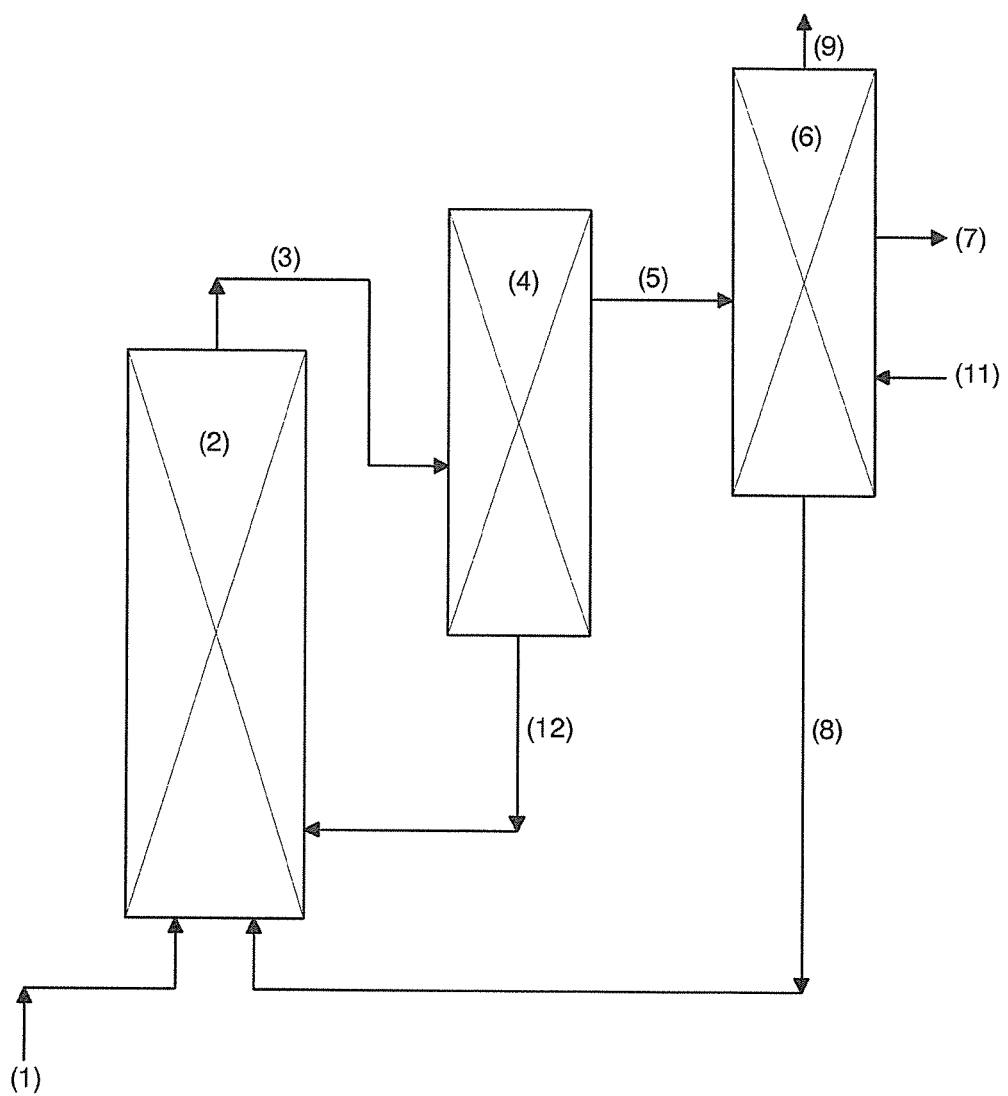
FIGS. 3 to 8 illustrate diagrammatic flow charts of embodiments of the process in accordance with the present disclosure.

A detailed description of embodiments of the present process is disclosed herein. However, it is to be understood that the disclosed embodiments are merely exemplary of the process and that the process may be embodied in various and alternative forms of the disclosed embodiments. Therefore, specific procedural, structural and functional details which are addressed in the embodiments disclosed herein are not to be interpreted as limiting, but merely as a basis for the claims and as a representative basis for teaching one skilled in the art to variously employ the present invention.

Unless specifically stated otherwise, all technical terms used herein have the meaning as commonly understood by those skilled in the art.

The designation of groups of the Periodic Table of the Elements as used herein is in accordance with the current IUPAC convention.

Moreover, unless specifically stated otherwise, the following expressions as used herein are understood to have the following meanings.

The expression "liquid stream" as used herein refers to a product or composition which is in the liquid state under the conditions of the processing step in which the stream is formed.

Correspondingly, the expression "vapor stream" as used herein refers to a product or composition which is in the gaseous state under the conditions of the processing step in which the stream is formed.

The expression "reaction zone" as used herein refers to at least one reactor or vessel in which methanol is carbonylated in the presence of a catalyst to form acetic acid at elevated pressure and temperature, i.e., the reactor(s) of a methanol producing plant.

The expression "flash zone" as used herein refers to at least one tank or vessel in which the reaction mixture obtained by carbonylating methanol in the presence of a catalyst to form acetic acid is at least partially depressurized and/or cooled to form a vapor stream and a liquid stream, i.e., the flash tank(s) in the reaction area of a methanol producing plant.

The expression "fractioning zone" as used herein refers to at least one fractioning or distillation column, i.e., the light ends distillation column(s) in the light ends recovery area of an acetic acid producing plant.

The expression "alkylimidazole" as used herein refers imidazole in which at least one and at most three of the hydrogen atoms is or are replaced by an alkyl group. In this context, the expression "alkyl group" refers to straight chain or branched saturated hydrocarbon moieties, mono- or polycyclic saturated hydrocarbon moieties, as well as combinations thereof. Moreover, the reference to "alkylimidazole" in the singular is intended to include instances in which a combination of two or more alkylimidazoles is employed.

The expressions "OAc" or "AcO" are used herein as abbreviations for the acetate anion, i.e., $H_3CC(=O)O^-$.

The expression "acac" is used herein as an abbreviation for acetoacetate anion, i.e., $H_3CC(=O)CH_2C(=O)O^-$.

Unless specifically indicated otherwise, the expression "wt. %" as used herein refers to the percentage by weight of a particular component in the referenced composition.

With respect to all ranges disclosed herein, such ranges are intended to include any combination of the mentioned upper and lower limits even if the particular combination is not specifically listed.

All publications, patent applications, and patents mentioned herein are incorporated by reference in their entirety. In the event of conflict, the present specification, including definitions, is intended to control.

The process in accordance with the present disclosure involves (a) carbonylating methanol in the presence of a catalyst in a reaction zone to obtain a reaction mixture (A) comprising acetic acid, hydrogen iodide, methyl iodide, water, and the catalyst;

(b) separating at least a part of the reaction mixture (A) in a flash zone to obtain a liquid stream ($B_L$) comprising the catalyst, and a vapor stream ($B_V$) comprising acetic acid, hydrogen iodide, methyl iodide and water, and withdrawing the vapor stream ($B_V$) from the flash zone;

(c) reacting the withdrawn vapor stream ($B_V$) with at least one alkylimidazole to obtain a composition (C); and (d) separating the acetic acid from the composition (C).

It has been found, surprisingly, that contacting the vapor stream ($B_V$) which is withdrawn from the flash zone with the alkylimidazole causes the alkylimidazole to react with hydrogen iodide and with methyl iodide, thus forming the corresponding iodide salts. Accordingly, the alkylimidazole acts as a scavenger of hydrogen iodide thereby reducing the amount of hydrogen iodide which may become entrained in the product stream. It has further been found, surprisingly, that the presence of the iodide salt in the composition (C) also has a significant and advantageous impact on the subsequent purification of acetic acid. In particular, it has been found that the iodide salts interact with hydrogen iodide and, thus, reduce the tendency of hydrogen iodide to vaporize, and to become entrained in the crude acetic acid product which is separated from the composition (C). The iodide salts themselves are high boiling and therefore become part of the liquid stream ($D_L$) in the fractioning zone where they inhibit or at least significantly reduce the tendency of hydrogen iodide to vaporize. In some embodiments, the inhibiting effect of iodide salt(s) on the vaporization of hydrogen iodide is essentially similar to that of a pentavalent Group 15 oxide such as triphenylphosphine oxide.

It has further been found, surprisingly, that the iodide salt or salts do not significantly increase, and in some embodiments even reduce, the tendency of water to vaporize from the bottom stream ($B_L$). In some embodiments, the inhibiting effect of the iodide salt or salts on the vaporization of water is similar to that of lithium iodide.

The carbonylation reaction in accordance with the present disclosure is performed in the presence of a carbonylation catalyst and optionally a catalyst stabilizer. Suitable carbonylation catalysts include those known in the acetic acid industry. Examples of suitable carbonylation catalysts include rhodium catalysts and iridium catalysts.

Suitable rhodium catalysts are described, for example, in U.S. Pat. No. 5,817,869. Suitable rhodium catalysts include rhodium metal and rhodium compounds. Preferably, the rhodium compounds are selected from the group consisting of rhodium salts, rhodium oxides, rhodium acetates, organorhodium compounds, coordination compounds of rhodium, the like, and mixtures thereof. More preferably, the rhodium compounds are selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H]Rh(CO)_2I_2$, the like, and mixtures thereof. Most preferably, the rhodium compounds are selected from the group consisting of $[H]Rh(CO)_2I_2$, $Rh(CH_3CO_2)_2$, the like, and mixtures thereof.

Suitable iridium catalysts are described, for example, in U.S. Pat. No. 5,932,764. Suitable iridium catalysts include iridium metal and iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3 \times 4H_2O$, $IrBr_3 \times 4H_2O$, $Ir_3(CO)_{12}$, $Ir_2O_3$, $IrO_2$, $Ir(acac)(CO)_2$, $Ir(acac)_3$, $Ir(OAc)_3$, $[Ir_3O(OAc)_6(H_2O)_3][OAc]$, and $H_2[IrCl_6]$. Preferably, the iridium compounds are selected from the group consisting of acetates, oxalates, acetoacetates, the like, and mixtures thereof. More preferably, the iridium compounds are acetates.

The iridium catalyst is preferably used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. More preferred co-catalysts are selected from the group consisting of ruthenium compounds and osmium compounds. Most preferred co-catalysts are ruthenium compounds. Preferably, the co-catalysts are acetates.

The reaction rate depends upon the concentration of the catalyst in the reaction mixture (A). The catalyst concentration normally is from about 1.0 mmol to about 100 mmol catalyst per liter (mmol/l) of (A). In some embodiments the catalyst concentration is at least 2.0 mmol/l, or at least 5.0 mmol/l, or at least 7.5 mmol/l. In some embodiments the catalyst concentration is at most 75 mmol/l, or at most 50 mmol/l, or at least 25 mmol/l. In particular embodiments, the catalyst concentration is from about 2.0 to about 75 mmol/l, or from about 2.0 to about 50 mmol/l, or from about 5.0 to about 25 mmol/l.

In some embodiments, the reaction is performed in the presence of a catalyst stabilizer. Suitable catalyst stabilizers include those known to the industry. In general, there are two types of catalyst stabilizers. The first type of catalyst stabilizer is metal iodide salt, i.e., a iodide of a metal of Group 1 or 2 such as lithium iodide. The second type of catalyst stabilizer is a non-salt stabilizer. Preferred non-salt stabilizers are pentavalent Group 15 oxides. See U.S. Pat. No. 5,817,869. Phosphine oxides are more preferred. Triphenylphosphine oxides are most preferred.

The amount of metal iodide, when used, generally is such that a concentration of from about 1 to about 20 wt. % (about 0.1 to about 1.75 M) of the metal iodide is present in the reaction mixture. More preferably, this optional component is present in the reaction mixture in an amount of from about 5 to about 10 wt. % which corresponds to a molarity range of from about 0.5 to about 1.0 M.

The amount of pentavalent Group 15 oxide, when used, generally is such that its concentration to rhodium is greater than about 60:1. Preferably, the concentration of the pentavalent Group 15 oxide to rhodium is from about 60:1 to about 500:1. In some embodiments, from about 0.1 to about 3 M of the pentavalent Group 15 oxide is present in the reaction mixture. More preferably, from about 0.15 to about 1.5 M, or from 0.25 to 1.2 M, of the pentavalent Group 15 oxide is present in the reaction mixture.

In other embodiments, the reaction is performed in the absence of a stabilizer selected from the group of metal iodides and pentavalent Group 15 oxides. In further embodiments, the catalyst stabilizer consists of the iodide salt or salts which are formed by reacting ($B_V$) with the alkylimidazole.

The carbonylation reaction is preferably performed in the presence of water. Preferably, the concentration of water which is present in the reaction zone is from about 2 wt. % to about 14 wt. % based on the total weight of the reaction mixture (A). More preferably, the water concentration is from about 2 wt. % to about 10 wt. %. Most preferably, the water concentration is from about 3 wt. % to about 8 wt. %.

The reaction is preferably performed in the presence of methyl acetate. Methyl acetate can be formed in situ. Optionally, methyl acetate can be added as a starting material to the reaction mixture. Preferably, the concentration of methyl acetate is from about 2 wt. % to about 20 wt. % based on the total weight of the reaction mixture (A). More preferably, the concentration of methyl acetate is from about 2 wt. % to about 16 wt. %. Most preferably, the concentration of methyl acetate is from about 2 wt. % to about 8 wt. %. Alternatively, methyl acetate or a mixture of methyl acetate and methanol from by-product streams of the hydrolysis/methanolysis of polyvinyl acetate can be used for the carbonylation reaction.

The reaction is performed in the presence of methyl iodide. Methyl iodide acts as a catalyst promoter. Preferably, the concentration of methyl iodide is from about 0.6 wt. % to about 36 wt. % based on the total weight of the reaction mixture (A). More preferably, the concentration of methyl iodide is from about 4 wt. % to about 24 wt. %. Most preferably, the concentration of methyl iodide is from about 6 wt. % to about 20 wt. %. Alternatively, methyl iodide can be generated in the carbonylation reactor or reaction zone by adding hydrogen iodide.

Hydrogen may also be fed into the reaction zone. Addition of hydrogen can enhance the carbonylation efficiency. Preferably, the concentration of hydrogen is from about 0.1 mol % to about 5 mol % of carbon monoxide in the reaction zone. More preferably, the concentration of hydrogen is from about 0.3 mol % to about 3 mol % of carbon monoxide in the reaction zone.

Methanol and carbon monoxide are fed to the carbonylation reactor or reaction zone. The methanol feed to the carbonylation reaction can come from a syngas-methanol facility or any other source. Methanol does not react directly with carbon monoxide to form acetic acid. It is converted to methyl iodide by the hydrogen iodide present in the reaction zone and then reacts with carbon monoxide and water to give acetic acid and regenerate hydrogen iodide. Carbon monoxide not only becomes part of the acetic acid molecule, but it also plays an important role in the formation and stability of the active catalyst.

The carbonylation reaction is preferably performed at a temperature of about 120° C. to about 250° C. More preferably, the reaction is performed at a temperature of about 150° C. to about 200° C.

The carbonylation reaction is preferably performed under a pressure of about 200 psig to about 2,000 psig. More preferably, the reaction is performed under a pressure of about 300 psig to about 500 psig.

While the process may be performed batch-wise, it is preferable to operate the process continuously. Thus, at least a part of the reaction mixture (A) which is obtained in the carbonylation reaction is withdrawn from the reaction zone and is separated, by a flash separation in the flash zone, to obtain a liquid stream ($B_L$) comprising the catalyst and, where present, the catalyst stabilizer, and a vapor stream ($B_V$) comprising the acetic acid, as well as hydrogen iodide, methyl iodide, and water. The liquid stream ($B_L$) is preferably recycled to the reaction zone.

The flash zone is preferably maintained at a pressure below that of the reaction zone, typically at a pressure of from about 10 to 100 psig. The flash zone is preferably maintained at a temperature of from about 100 to 160° C.

The vapor stream ($B_V$) is withdrawn from the flash zone, and the withdrawn stream is then reacted with at least one alkylimidazole whereby at least a part of the alkylimidazole(s) react(s) with at least a part of the hydrogen iodide and/or methyl iodide component of ($B_V$) to form the corresponding iodide salt or salts.

In accordance with some embodiments, the alkylimidazole is a compound of formula (I)

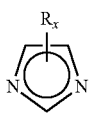

wherein x is 1, 2 or 3, and each R independently is $C_1$-$C_6$-alkyl, i.e., methyl, ethyl, propyl, 1-methylethyl, 1-butyl, 2-butyl, 1-(2-methyl)propyl, 2-(2-methyl)propyl, 1-pentyl, 2-pentyl, 3-pentyl, 1-(2-methyl)butyl, 1-(3-methyl)butyl, 2-(2-methyl)butyl, 2-(3-methyl)butyl, 1-(2,2-dimethyl)propyl, 1-hextyl, 2-hextyl, 3-hextyl, 1-(2-methyl)pentyl, 1-(3-methyl)pentyl, 1-(4-methyl)pentyl, 2-(2-methyl)pentyl, 2-(3-methyl)pentyl, 2-(4-methyl)pentyl, 3-(2-methyl)pentyl, 1-(2,2-dimethyl)butyl, 1-(2,3-dimethyl)butyl, 1-(3,3-dimethyl)butyl, 2-(2,3-dimethyl)butyl, 1-(2-ethyl)butyl, and 2-(2-ethyl)butyl.

In further embodiments, the alkylimidazole is a compound of formula (Ia)

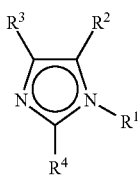

wherein
$R^1$ is hydrogen, or $C_1$-$C_6$-alkyl, in particular hydrogen or $C_1$-$C_4$-alkyl, i.e., hydrogen, methyl, ethyl, propyl, 1-methylethyl, 1-butyl, 2-butyl, 1-(2-methyl)propyl, and 2-(2-methyl)propyl; and $R^2$, $R^3$ and $R^4$, each independently, is hydrogen, or $C_1$-$C_2$-alkyl, i.e., hydrogen, methyl or ethyl;
and wherein at least one of $R^1$, $R^2$, $R^3$ and $R^4$ is different from hydrogen, and at least one of $R^1$, $R^2$, $R^3$ and $R^4$ is hydrogen.

In yet further embodiments, the alkylimidazole is 1-methylimidazole, 1-ethylimidazole, 1-propylimidazole, 1-isopropylimidazole, 1-(1-butyl)imidazole, 1-(2-butyl)imidazole, 1-isobutylimidazole, 1-tert-butylimidazole, 3-methylimidazole, 3-ethylimidazole, 4-methylimidazole, 4-ethylimidazole, 1,4-dimethylimidazole, 1,4-diethylimidazole, 1-ethyl-4-methylimidazole, 4-ethyl-1-methylimidazole, 2-methyl-1-propylimidazole, 4-methyl-1-propylimidazole, 5-methyl-1-propylimidazole, 2,4-dimethyl-1-propylimidazole, 2,5-dimethyl-1-propylimidazole, 1-isopropyl-2-methylimidazole, 1-isopropyl-4-methylimidazole, 1-isopropyl-5-methylimidazole, 2,4-dimethyl-1-isopropylimidazole, 2,5-dimethyl-1-isopropylimidazole, 1-(1-butyl)-2-methylimidazole, 1-(1-butyl)-4-methylimidazole, 1-(1-butyl)-5-methylimidazole, 1-(1-butyl)-2,4-dimethylimidazole, 1-(1-butyl)-2,5-dimethylimidazole, 1-(2-butyl)-2-methylimidazole, 1-(2-butyl)-4-methylimidazole, 1-(2-butyl)-5-methylimidazole, 1-(2-butyl)-2,4-dimethylimidazole, 1-(2-butyl)-2,5-dimethylimidazole, 1-isobutyl-2-methylimidazole, 1-isobutyl-4-methylimidazole, 1-isobutyl-5-methylimidazole, 2,4-dimethyl-1-isobutylimidazole, 2,5-dimethyl-1-isobutylimidazole, 1-tert-butyl-2-methylimidazole, 1-tert-butyl-4-methylimidazole, 1-tert-butyl-5-methylimidazole, 1-tert-butyl-2,4-dimethylimidazole, or 1-tert-butyl-2,5-dimethylimidazole.

The reaction of the alkylimidazole with the vapor stream ($B_V$) causes the alkylimidazole to form a iodide salt with the hydrogen iodide and/or methyl iodide contained in ($B_V$). Typically, the reaction of the alkylimidazole with hydrogen iodide or methyl iodide is rapid and is normally quantitative at a temperature of about 20° C. Generally, the reaction takes place when the alkylimidazole is added to the vapor stream ($B_V$) and, thus, is brought into contact with hydrogen iodide and methyl iodide.

The amount of alkylimidazole which is added to the vapor stream ($B_V$) is generally not critical so long as the alkylimidazole is added in an effective amount. An effective amount in this context is the amount of alkylimidazole which is capable of scavenging at least a part of the hydrogen iodide which is present in the vapor stream ($B_V$), either by way of forming the corresponding iodide salt or by way of an interaction of the hydrogen iodide with a iodide salt formed from the alkylimidazole and either methyl iodide or hydrogen iodide.

In some embodiments, the amount of alkylimidazole which is added to the vapor stream ($B_V$) is adjusted depending on the hydrogen iodide and methyl iodide content of ($B_V$). In some of these embodiments, the alkylimidazole is employed in an amount of at least about 0.01 mol per mol methyl iodide. In alternative embodiments, at least about 0.05 mol alkylimidazole, or at least about 0.1 mol alkylimidazole, or at least about 0.5 mol alkylimidazole, per mol methyl iodide is added. Generally, it is not detrimental to the subsequent separation and purification of the acetic acid product if the molar amount of alkylimidazole exceeds the molar amount in which methyl iodide is present, even if the excess in which the alkylimidazole is added is significant so long as the boiling point of the alkylimidazole is sufficiently higher than the boiling point of the crude acetic acid which is withdrawn from the fractioning zone. Normally, the boiling point of the alkylimidazole in degree Celsius is sufficiently higher when the boiling point is at least 15°, or at least 30°, or at least 50°, above the boiling point of the crude acetic acid in degree Celsius. In particular variants of these embodiments, the alkylimidazole is added to the vapor stream ($B_V$) in an amount of from about 0.01 to about 2 mol per mol methyl iodide. In alternative variants, the amount of alkylimidazole is from about 0.01 to about 1.5 mol, or from about 0.01 to about 1.2 mol, or from about 0.01 to about 0.9 mol, per mol methyl iodide. In further alternative embodiments, the amount of alkylimidazole is from about 0.1 to about 1.5 mol, or from about 0.1 to about 1.2 mol, or from about 0.1 to about 0.9 mol, per mol methyl iodide.

In other embodiments, the alkylimidazole is employed in an amount of at least about 0.1 mol per mol hydrogen iodide. In alternative embodiments, at least about 0.5 mol alkylimidazole, or at least about 1 mol alkylimidazole, or at least about 1.5 mol alkylimidazole, per mol hydrogen iodide is added. Generally, it is not detrimental to the subsequent separation and purification of the acetic acid product if the molar amount of alkylimidazole exceeds the molar amount in which hydrogen iodide is present, even if the excess in which the alkylimidazole is added is significant so long as the boiling point of the alkylimidazole is sufficiently higher than the boiling point of the crude acetic acid which is withdrawn from the fractioning zone. In particular variants of these embodiments, the alkylimidazole is added to the vapor stream ($B_V$) in an amount from about 0.1 to about 1.5 mol per mol hydrogen iodide. In alternative variants, the amount of alkylimidazole is from about 0.1 to about 1.3 mol, or from about 0.1 to about 1.1 mol, per mol hydrogen iodide. In further alternative embodiments, the amount of alkylimidazole is from about 0.5 to about 3 mol, or from about 0.5 to about 2 mol, or from about 0.5 to about 1.5 mol, per mol hydrogen iodide.

In further embodiments, the alkylimidazole is reacted with the vapor stream ($B_V$) in an amount sufficient to establish a concentration of no more than about 20 wt. % of the iodide salt in the composition (C). In alternative embodiments, the alkylimidazole is reacted with ($B_V$) in an amount sufficient to establish a concentration of no more than about 15 wt. %, or no more than about 12 wt. %, or no more than about 10 wt. %, of the iodide salt in the composition (C). In other embodiments, the alkylimidazole is reacted with the vapor stream ($B_V$) in an amount sufficient to establish a concentration of at least about 0.5 wt. % of the iodide salt in the reaction composition (C). In alternative embodiments, the alkylimidazole is reacted with ($B_V$) in an amount sufficient to establish a concentration of at least about 1 wt. %, or at least about 2.5 wt. %, or at least about 4 wt. %, of the iodide salt in the composition (C). In particular embodiments, the alkylimidazole is reacted with the vapor stream ($B_V$) in an amount sufficient to establish a concentration of from about 0.5 wt. % to about 20 wt. % of the iodide salt in the composition (C). In alternative embodiments, the alkylimidazole is reacted with ($B_V$) in an amount sufficient to establish a concentration of from about 1 wt. % to about 20 wt. %, or from about 2.5 wt. % to about 20 wt. %, or from about 4 wt. % to about 20 wt. %, of the iodide salt in the composition (C). In alternative embodiments, the alkylimidazole is reacted with ($B_V$) in an amount sufficient to establish a concentration of from about 0.5 wt. % to about 15 wt. %, or from about 1 wt. % to about 15 wt. %, or from about 2.5 wt. % to about 15 wt. %, or from about 4 wt. % to about 15 wt. %, of the iodide salt in the composition (C). In alternative embodiments, the alkylimidazole is reacted with ($B_V$) in an amount sufficient to establish a concentration of from about 0.5 wt. % to about 12 wt. %, or from about 1 wt. % to about 12 wt. %, or from about 2.5 wt. % to about 12 wt. %, or from about 4 wt. % to about 12 wt. %, of the iodide salt in the composition (C).

In general, the alkylimidazole is added to the vapor stream ($B_V$) at any time after the stream has been withdrawn from the flash zone, prior to and/or at the time ($B_V$) is contained in the fractioning zone. Both the iodide salt, as well as optionally unreacted alkylimidazole, which is present in the composition (C) are high boiling. Therefore, the iodide salt, as well as optionally unreacted alkylimidazole, which are present in the composition (C) which reaches, or is formed in, the fractioning zone, will become part of a liquid stream ($D_L$) which is generated in the fractioning zone as a bottom product.

The liquid stream ($D_L$) can be recycled to the reaction zone. In some embodiments, the liquid stream ($D_L$) is recycled by firstly introducing ($D_L$) into the flash zone. In these embodiments, the liquid stream ($D_L$) and the liquid stream ($B_L$) which is formed in the flash zone are combined, and the combined streams ($D_L$) and ($B_L$) are, in whole or in part, recycled to the reaction zone.

The recycled liquid stream ($D_L$), or the combined streams ($D_L$) and ($B_L$), introduce(s) the iodide salt as well as any optionally present unreacted alkylimidazole into the reaction zone and, consequently, into the reaction mixture (A).

In certain embodiments, the addition of alkylimidazole to the vapor stream ($B_V$) is adjusted to establish a steady state concentration of no more than about 20 wt. % of the iodide salt in the reaction mixture (A). In alternative embodiments, the alkylimidazole is reacted with ($B_V$) in an amount sufficient to establish a steady state concentration of no more than about 17 wt. %, or no more than about 15 wt. %, or no more than about 12 wt. %, of the iodide salt in the reaction mixture (A).

In other embodiments, the alkylimidazole is reacted with the vapor stream ($B_V$) in an amount sufficient to establish a steady state concentration of at least about 2 wt. % of the iodide salt in the reaction mixture (A). In alternative embodiments, the alkylimidazole is reacted with ($B_V$) in an amount sufficient to establish a steady state concentration of at least about 5 wt. %, or at least about 7 wt. %, of the iodide salt in the reaction mixture (A).

In particular embodiments, the alkylimidazole is reacted with the vapor stream ($B_V$) in an amount sufficient to establish a steady state concentration from about 2 wt. % to about 20 wt. % of the iodide salt in the reaction mixture (A). In alternative embodiments, the alkylimidazole is reacted with ($B_V$) in an amount sufficient to establish a steady state concentration of from about 5 wt. % to about 20 wt. %, or from about 7 wt. % to about 20 wt. %, of the iodide salt in the reaction mixture (A). In alternative embodiments, the alkylimidazole is reacted with ($B_V$) in an amount sufficient to establish a steady state concentration of from about 2 wt. % to about 17 wt. %, or from about 5 wt. % to about 17 wt. %, or from about 7 wt. % to about 17 wt. %, of the iodide salt in the reaction mixture (A). In alternative embodiments, the alkylimidazole is reacted with ($B_V$) in an amount sufficient to establish a steady state concentration of from about 2 wt. % to about 15 wt. %, or from about 5 wt. % to about 15 wt. %, or from about 7 wt. % to about 15 wt. %, of the iodide salt in the reaction mixture (A). In alternative embodiments, the alkylimidazole is reacted with ($B_V$) in an amount sufficient to establish a steady state concentration of from about 2 wt. % to about 12 wt. %, or from about 5 wt. % to about 12 wt. %, or from about 7 wt. % to about 12 wt. %, of the iodide salt in the reaction mixture (A).

While it was known in the art that iodide salts of alkylimidazoles can be employed as catalyst stabilizers, the process in accordance with the present disclosure differs from the prior art procedures at least in that the iodide salts of the alkylimidazoles are generated in situ and downstream of the reaction area, i.e., downstream of the reaction zone and the flash zone. Moreover, the process in accordance with the present disclosure yields advantages which could not have been foreseen.

The alkylimidazole which is added to the vapor stream ($B_V$), as well as the iodide salt which is formed by reacting the alkylimidazole with the vapor stream ($B_V$), act as scavenger for hydrogen iodide in the fractioning zone, thus reducing the amount of hydrogen iodide which becomes entrained in the product stream ($D_P$). Consequently, side reactions which cause the formation of undesirable long chain alkyl iodide contaminants in the product stream ($D_P$) are significantly reduced. Additionally, the reduced amounts of hydrogen iodide in the product stream ($D_P$) alleviate corrosion and engineering problems. Moreover, the iodide salt acts as a catalyst stabilizer. Therefore, problems due to catalyst losses or deposits of deactivated catalyst are reduced or may even be avoided. Also surprisingly, in contrast to metal iodides, the iodide salt which is formed by reacting the vapor stream ($B_V$) with the alkylimidazole reduces the tendency of hydrogen iodide to vaporize while, at the same time not, or not significantly, affecting the tendency of water to vaporize.

The beneficial effect of the iodide salt on the vaporization of hydrogen iodide is not restricted to the fractioning zone. Rather, as the iodide salt becomes part of the reaction mixture (A), its presence equally reduces the tendency of hydrogen iodide to vaporize therefrom, thus reducing the amount of hydrogen iodide which is present in the vapor stream ($B_V$). Therefore, upon continuous operation of the process, the amount of alkylimidazole which is added to the vapor stream ($B_V$) normally will decrease as steady state conditions are achieved. Under steady state conditions, the amount of alkylimidazole which is added to the vapor stream ($B_V$) will normally be reduced to amounts necessary to maintain the desired steady state concentration of the iodide salt(s).

In general, the alkylimidazole can be added to the vapor stream ($B_V$) either batch-wise or continuously. In some embodiments, the alkylimidazole will be added batch-wise throughout the process. In other embodiments, the alkylimidazole will be added continuously until the desired steady state concentration of iodide salt in the reaction mixture (A) is established, and will be added continuously or batch-wise thereafter.

DETAILED DESCRIPTION OF THE DRAWINGS

FIG. 1 sets forth some of the interrelated reactions and equilibria believed to be involved in the carbonylation of methanol in the presence of a rhodium catalyst. Those having ordinary skill in the particular art will appreciate that further reactions and equilibria are involved and that the reproduced reactions are merely an illustration of the complexity of the multiplicity of interrelated reactions, by-products and equilibria.

FIG. 2 illustrates a diagrammatic flow chart of a prior art process for carbonylating alcohol in a non-aqueous ionic liquid as disclosed in U.S. Pat. No. 7,115,774. The reactants and the catalyst are fed to the reaction zone (2) via line (1), where they form the reaction mixture. The reaction mixture is withdrawn from the reaction zone (2) and is transferred via line (3) to a flash zone (4) where it is depressurized. The gas released upon depressurization is taken off through line (10) and is returned into the reaction zone (2) after recompression. The effluent from the flash zone is conveyed to the fractioning zone (6) via line (5), where it is separated into an overhead product comprising unreacted methanol and methyl iodide, crude acetic acid, and a polar phase comprising the catalyst and the ionic liquid. The overhead product is withdrawn via line (9) and is recycled to the reaction zone. Crude acetic acid is withdrawn via line (7) for further purification (not shown). The polar phase comprising the catalyst and the ionic liquid is withdrawn via line (8) and is returned to the reaction zone (2).

FIG. 3 illustrates a diagrammatic flow chart of a first embodiment of the process in accordance with the present disclosure. The reactants and the catalyst are fed to the reaction zone (2) via one or more lines, collectively represented by line (1), where they form the reaction mixture (A). At least a part of the reaction mixture (A) is withdrawn from the reaction zone (2) and is transferred via line (3) to the flash zone (4) where it is depressurized to form a liquid stream ($B_L$) comprising the catalyst, and a vapor stream ($B_V$) comprising acetic acid, hydrogen iodide, methyl iodide and water. The liquid stream ($B_L$) is withdrawn and is recycled to the reaction zone via line (12). The vapor stream ($B_V$) is conveyed via line (5) to the fractioning zone (6) where it forms the composition (C) with the alkylimidazole which is fed to the fractioning zone (6) via line (11). The composition (C) is separated in the fractioning zone (6) to obtain crude acetic acid as a product stream ($D_P$), a liquid stream ($D_L$) comprising the iodide salt and, optionally, an overhead fraction comprising unreacted methanol and methyl iodide. Crude acetic acid is withdrawn via line (7) for further purification (not shown). The liquid stream ($D_L$) comprising the iodide salt is withdrawn via line (8) and is returned to the reaction zone (2). The optional overhead fraction comprising unreacted methanol and methyl iodide is withdrawn via line (9) and is subjected to phase separation and/or is returned to the reaction zone (not shown).

Figure 4:
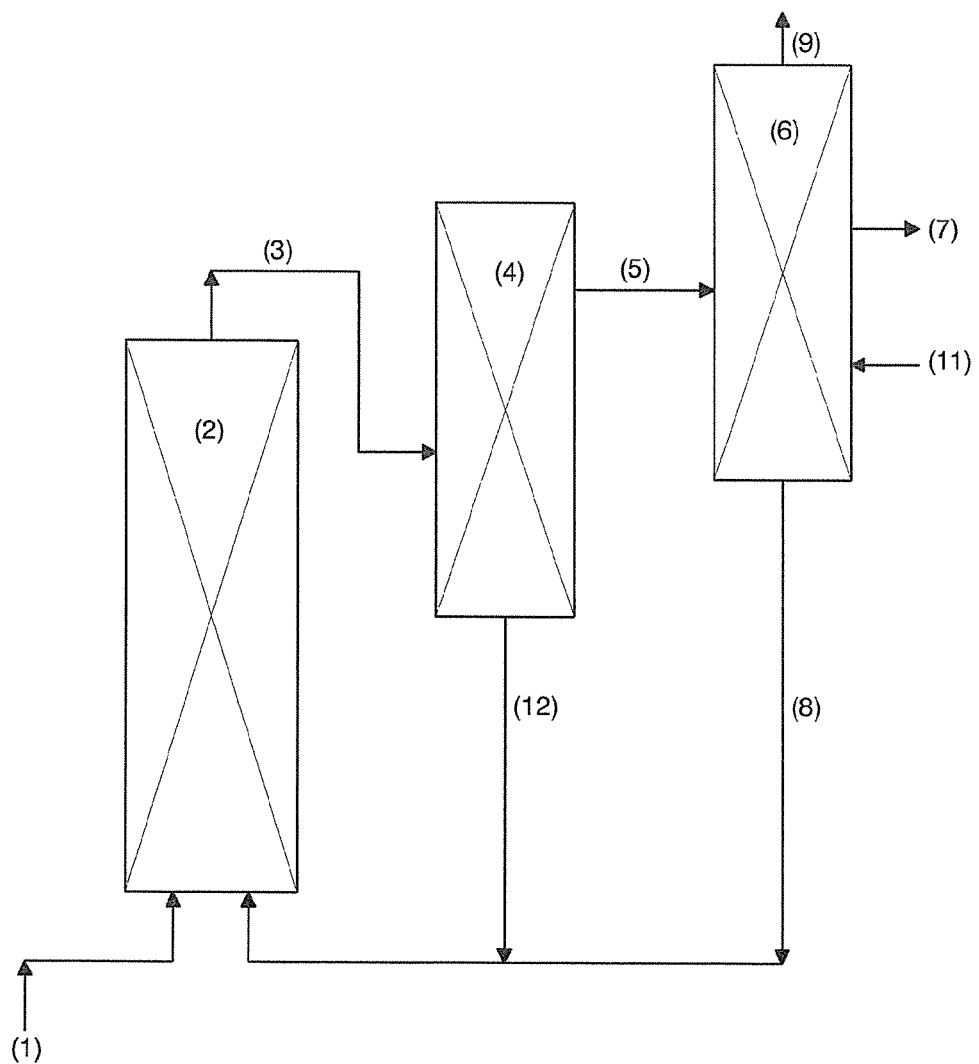

FIG. 4 illustrates a diagrammatic flow chart of a second embodiment of the process in accordance with the present disclosure. The second embodiment is a variation of the embodiment illustrated in FIG. 3. In this second embodiment, the liquid stream ($B_L$) comprising the catalyst which is withdrawn from the flash zone (4) via line (12) and the liquid stream ($D_L$) comprising the iodide salt which is withdrawn from the fractioning zone (6) via line (8) are combined, and the combined streams ($B_L$) and ($D_L$) are recycled to the reaction zone (2).

Figure 5:
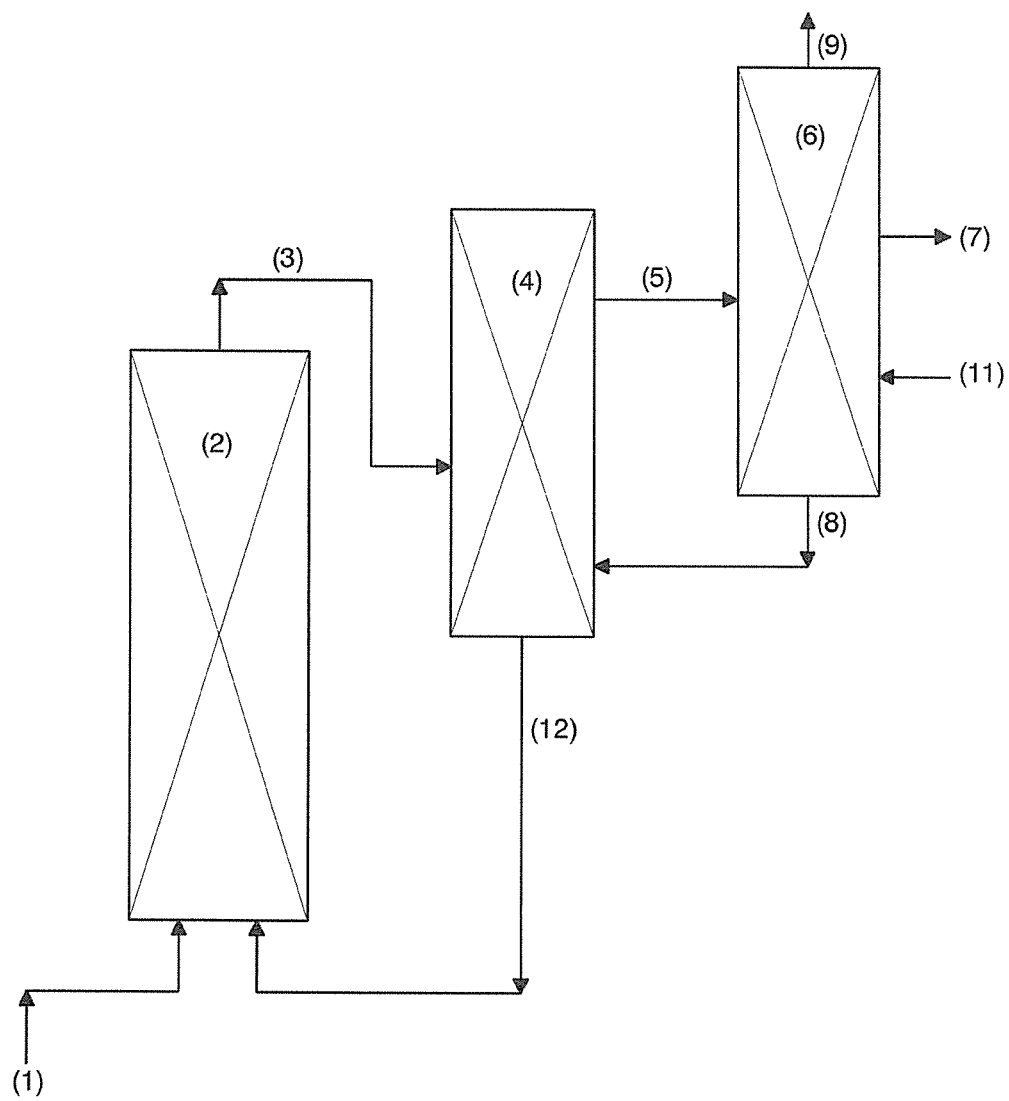

FIG. 5 illustrates a diagrammatic flow chart of a third embodiment of the process in accordance with the present disclosure. The third embodiment also is a variation of the embodiment illustrated in FIG. 3. In this third embodiment, the liquid stream ($D_L$) comprising the iodide salt which is withdrawn from the fractioning zone (6) via line (8) is recycled to the flash zone (4) where it combines with the liquid stream ($B_L$) comprising the catalyst. The combined liquid streams ($B_L$) and ($D_L$) are withdrawn from the flash zone (4) via line (12) and are recycled to the reaction zone (2).

Figure 6:
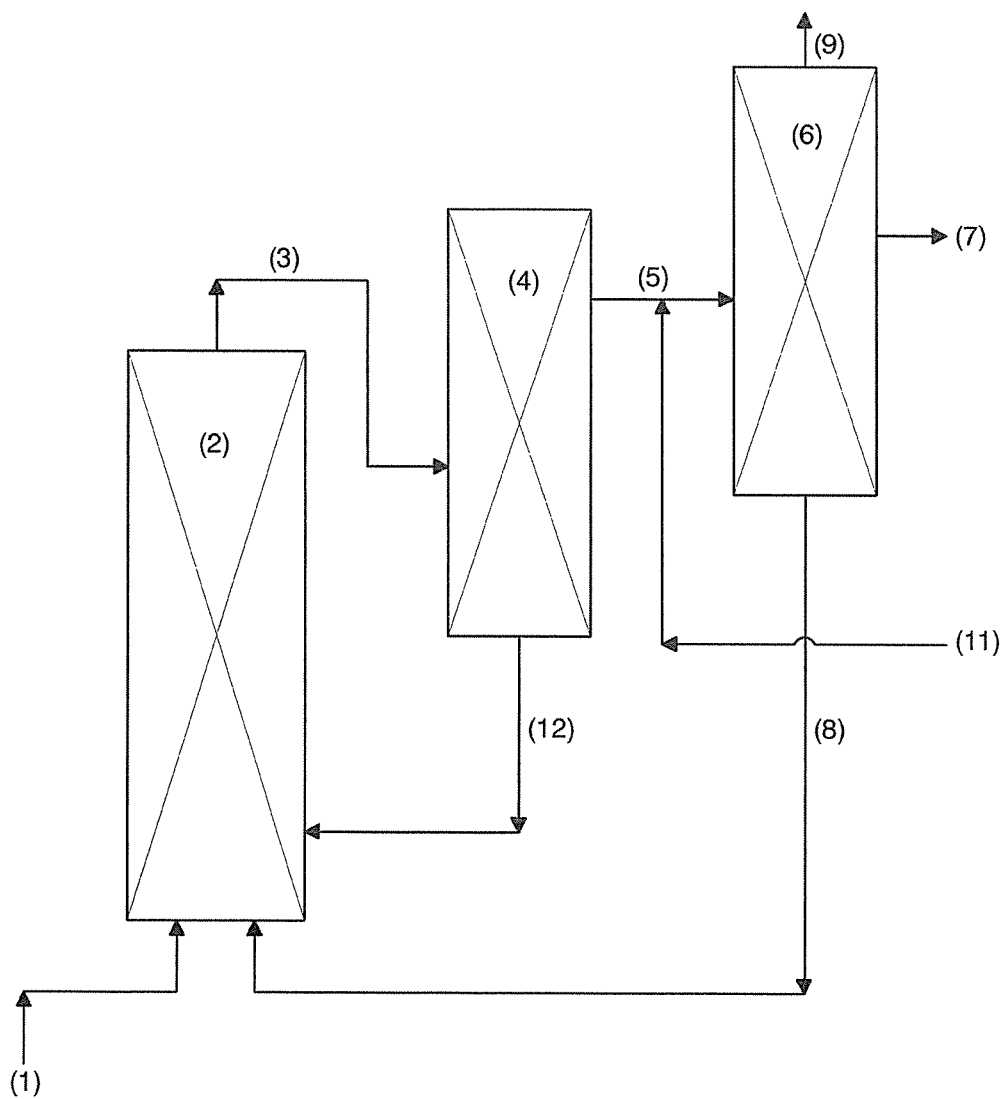

FIG. 6 illustrates a diagrammatic flow chart of a fourth embodiment of the process in accordance with the present disclosure. The fourth embodiment also is a variation of the embodiment illustrated in FIG. 3. In this fourth embodiment, the composition (C) is formed by adding the alkylimidazole to the vapor stream ($B_V$) after ($B_V$) has been withdrawn from the flash zone (4) but before it enters the fractioning zone (6), i.e., by injecting the alkylimidazole into line (5).

Figure 7:
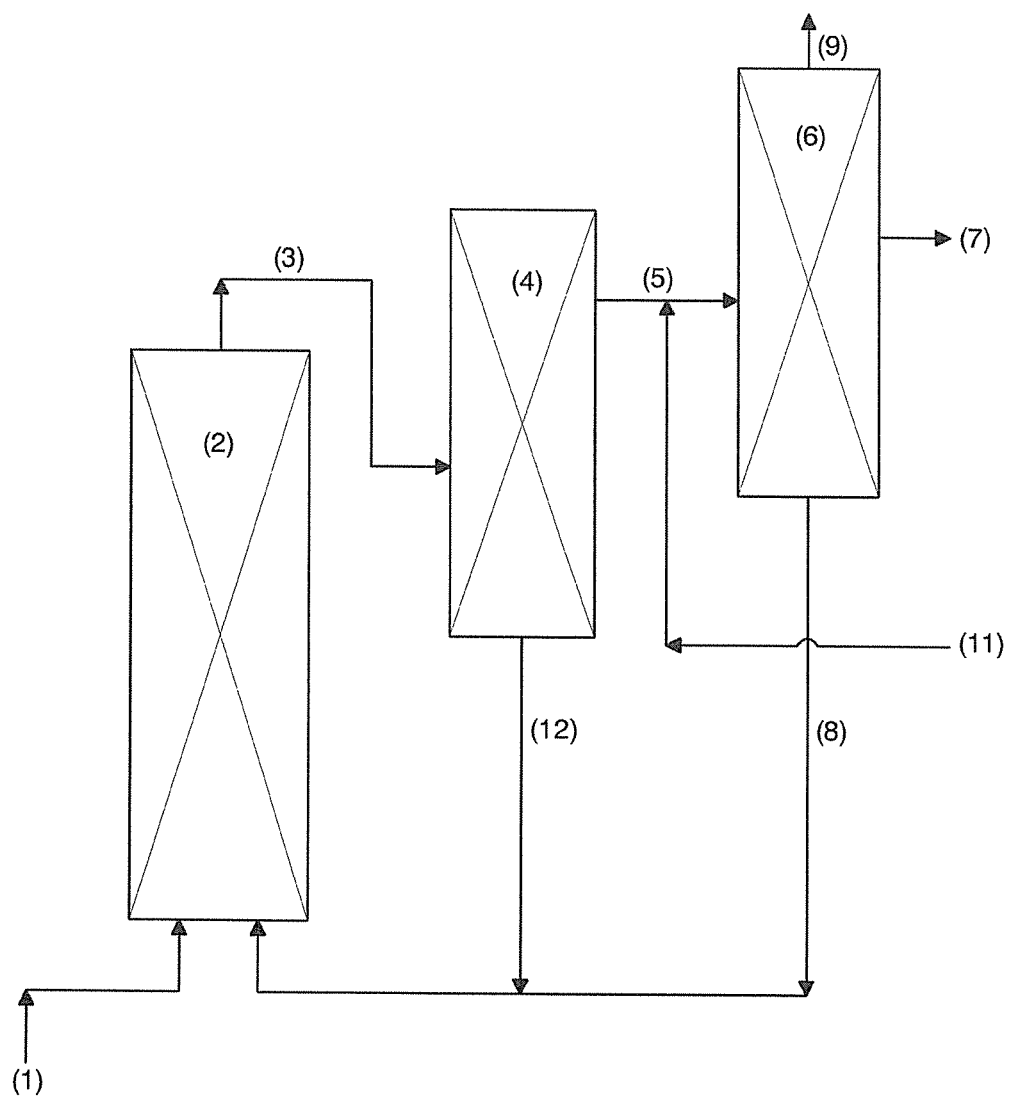

FIG. 7 illustrates a diagrammatic flow chart of a fifth embodiment of the process in accordance with the present disclosure. The fifth embodiment is a variation of the embodiment illustrated in FIG. 6. Again, the composition (C) is formed by adding the alkylimidazole to the vapor stream ($B_V$) after ($B_V$) has been withdrawn from the flash zone (4) but before it enters the fractioning zone (6), i.e., by injecting the alkylimidazole into line (5). After separating the composition (C) in the fractioning zone (6), the liquid stream ($B_L$) comprising the catalyst which is withdrawn from the flash zone (4) via line (12) and the liquid stream ($D_L$) comprising the iodide salt which is withdrawn from the fractioning zone (6)

via line (8) are combined, and the combined streams ($B_L$) and ($D_L$) are recycled to the reaction zone (2).

Figure 8:
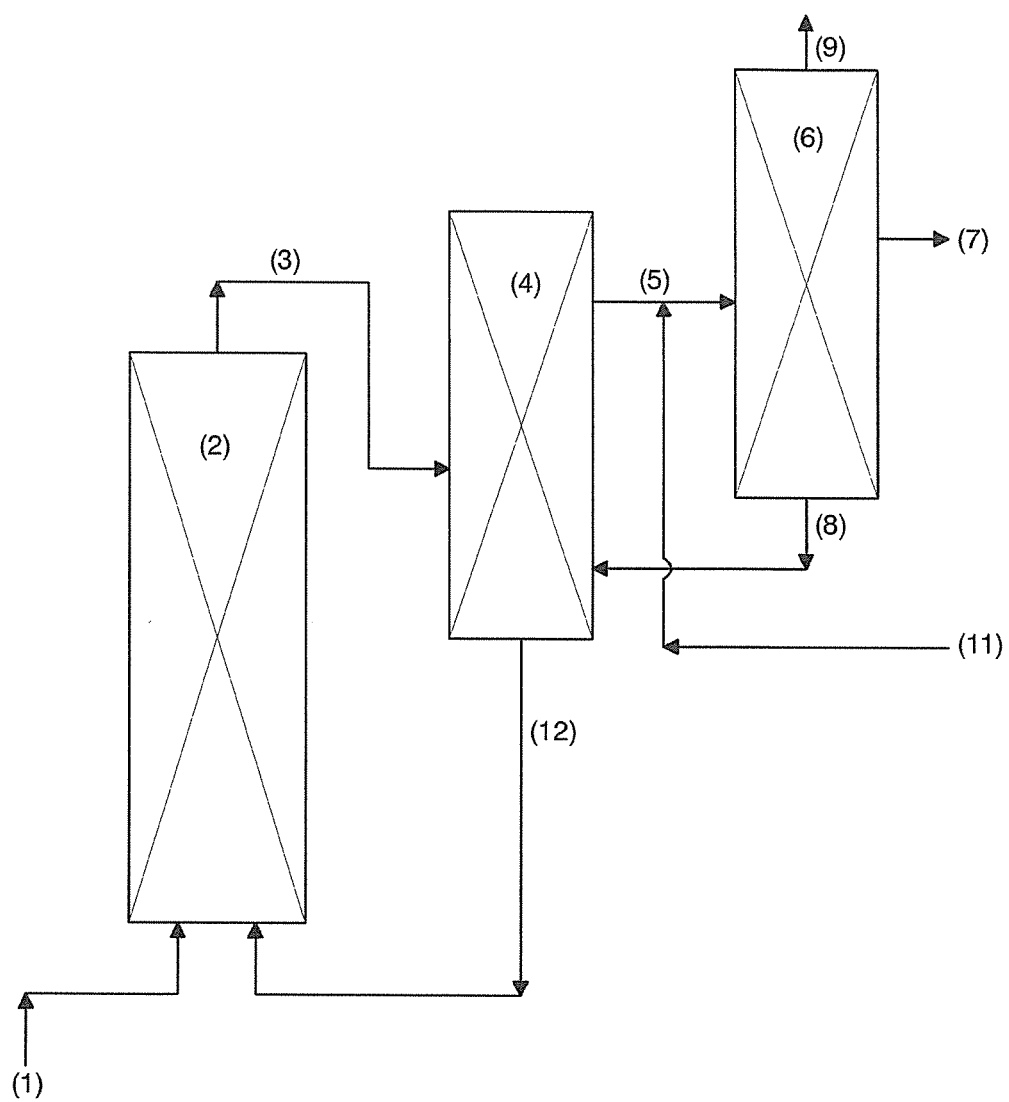

FIG. 8 illustrates a diagrammatic flow chart of a sixth embodiment of the process in accordance with the present disclosure. The sixth embodiment also is a variation of the embodiment illustrated in FIG. 6. Again, the composition (C) is formed by adding the alkylimidazole to the vapor stream ($B_V$) after ($B_V$) has been withdrawn from the flash zone (4) but before it enters the fractioning zone (6), i.e., by injecting the alkylimidazole into line (5). The composition (C) is separated in the fractioning zone (6). The liquid stream ($D_L$) comprising the iodide salt which is withdrawn from the fractioning zone (6) via line (8) is recycled to the flash zone (4) where it combines with the liquid stream ($B_L$) comprising the catalyst. The combined liquid streams ($B_L$) and ($D_L$) are withdrawn from the flash zone (4) via line (12) and are recycled to the reaction zone (2).

Figure 9:
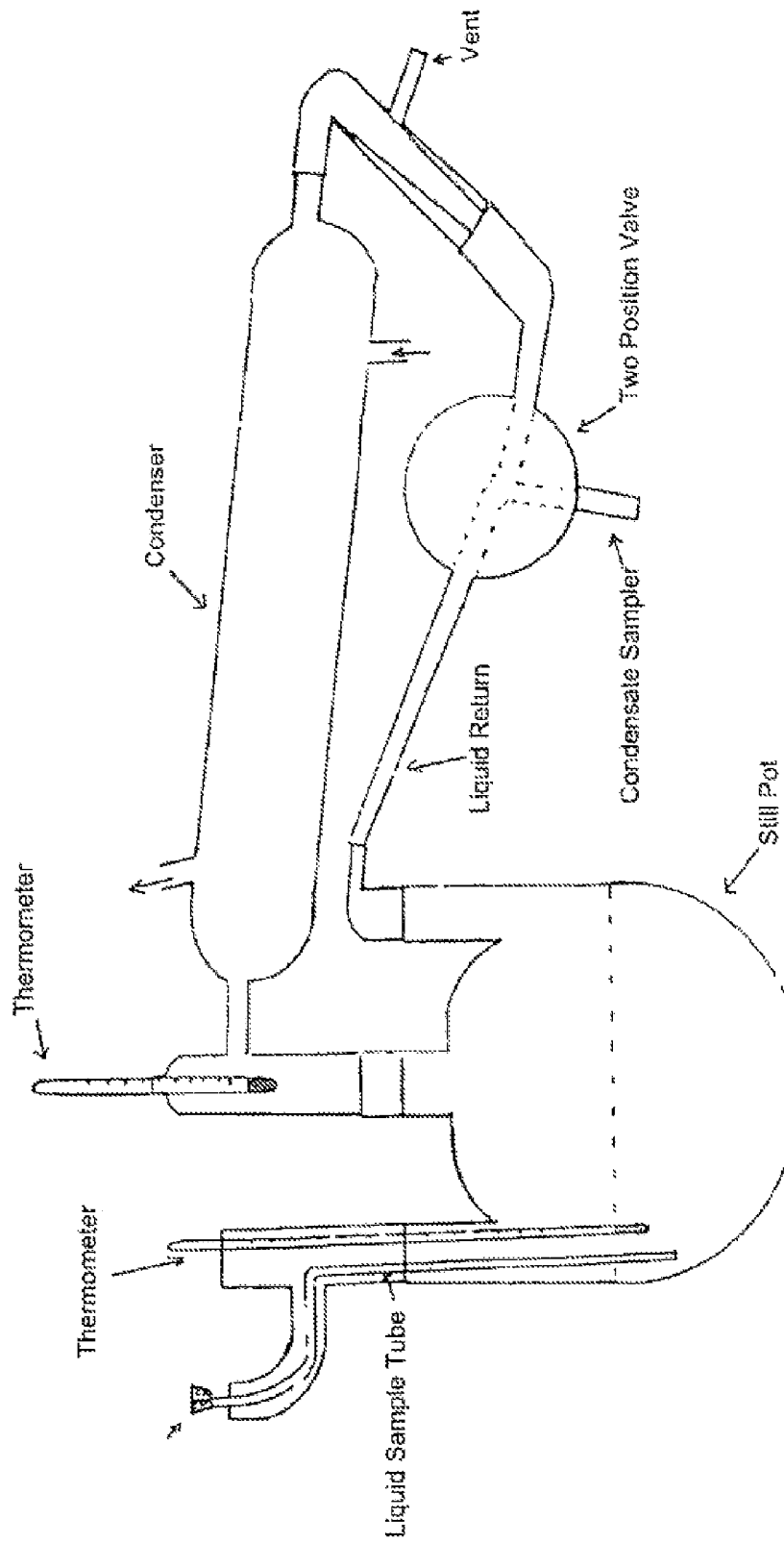
FIGS. 9 and 10 illustrate two recirculation apparatus for investigating the vapor liquid equilibrium (E).

FIG. 9 illustrates a diagrammatic first recirculation apparatus (Apparatus 1) for investigating the vapor liquid equilibrium (VLE). The apparatus comprises a 3-neck round-bottomed flask (Still Pot). The first neck is equipped with a tube (Liquid Sample Tube) for adding components to the liquid, or withdrawing samples from the liquid contained in the flask, and a thermometer measuring the temperature of the liquid contained in the flask. The second neck is equipped with a reflux/distillation head, and with a thermometer measuring the temperature of the vapor phase. The vapor is condensed in a condenser, and the condensate is conveyed back to the flask via a liquid return (Liquid Return) to the third neck of the flask. The liquid return is equipped with a vent (Vent) and a two position valve (Two Position Valve) for withdrawing samples of the condensate.

Figure 10:
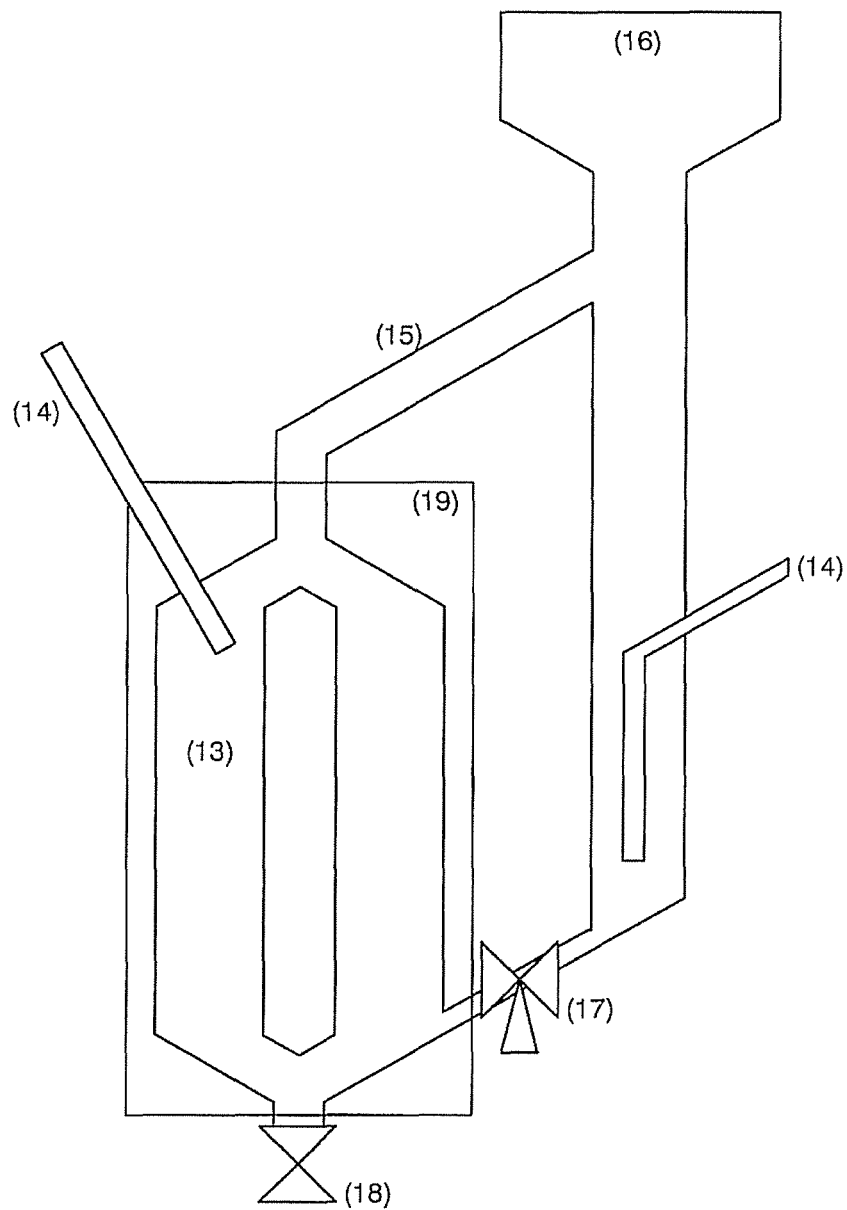

FIG. 10 illustrates a diagrammatic second recirculation apparatus (Apparatus 2) for investigating the vapor liquid equilibrium (VLE). The apparatus comprises a dual chambered circulation volume (13) as the still. The still is equipped with a recirculation line (15) which, in turn, connects to a condenser (16) and comprises a two position valve (17) for sampling the condensate. Additionally, the still is equipped with a bottom tap (18) for sampling the liquid. The still is enclosed by heating and insulating means (19). Both, the still (13) and the recirculation line (15) are provided with thermowells with thermocouples (14) connected to a temperature control unit (not shown).

Figure 11:
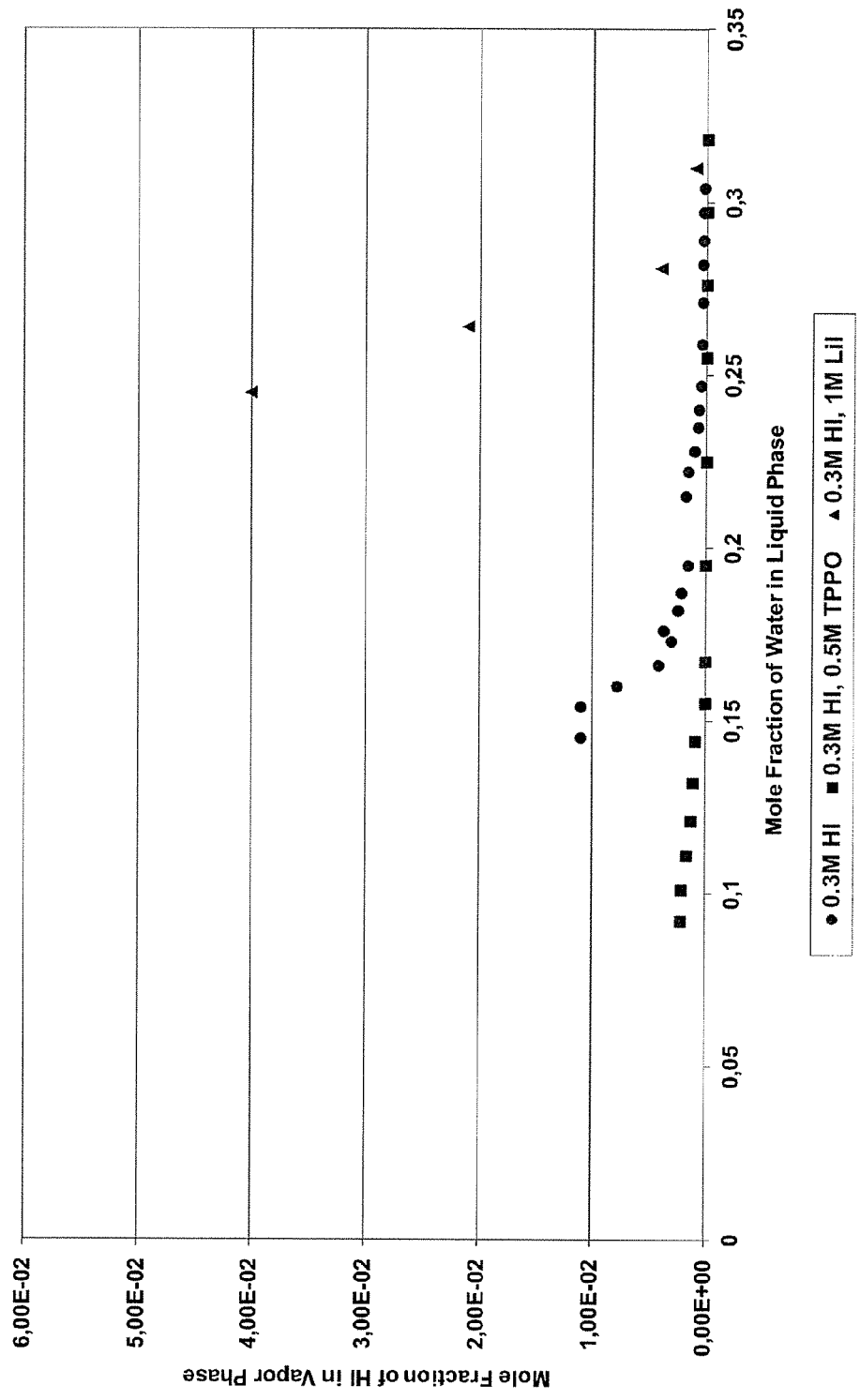
FIG. 11 depicts the results of investigations into the impact of triphenylphosphine oxide and lithium iodide on the VLE of hydrogen iodide in aqueous acetic acid.

FIG. 11 shows that the presence of 1M lithium iodide increases the volatility of hydrogen iodide whereas 0.5M triphenylphosphine oxide reduces the volatility of hydrogen iodide.

Figure 12:
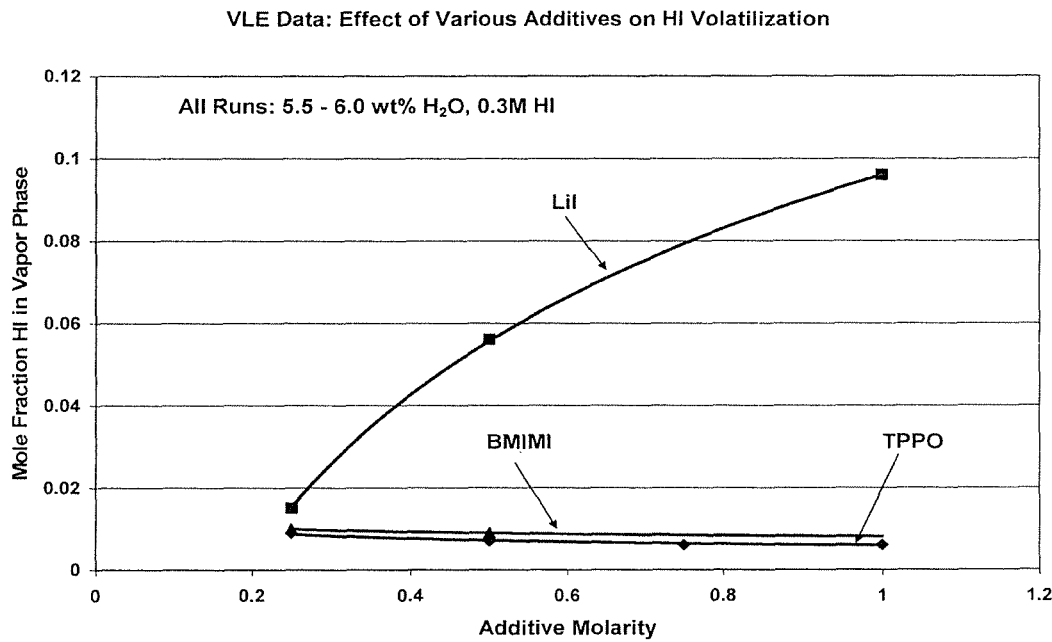
FIG. 12 depicts the results of investigations into the impact of triphenylphosphine oxide, lithium iodide, and 1-butyl, 3-methylimidazolium iodide on the VLE of hydrogen iodide in acetic acid comprising 5.5-6 wt. % of water.
Figure 13:
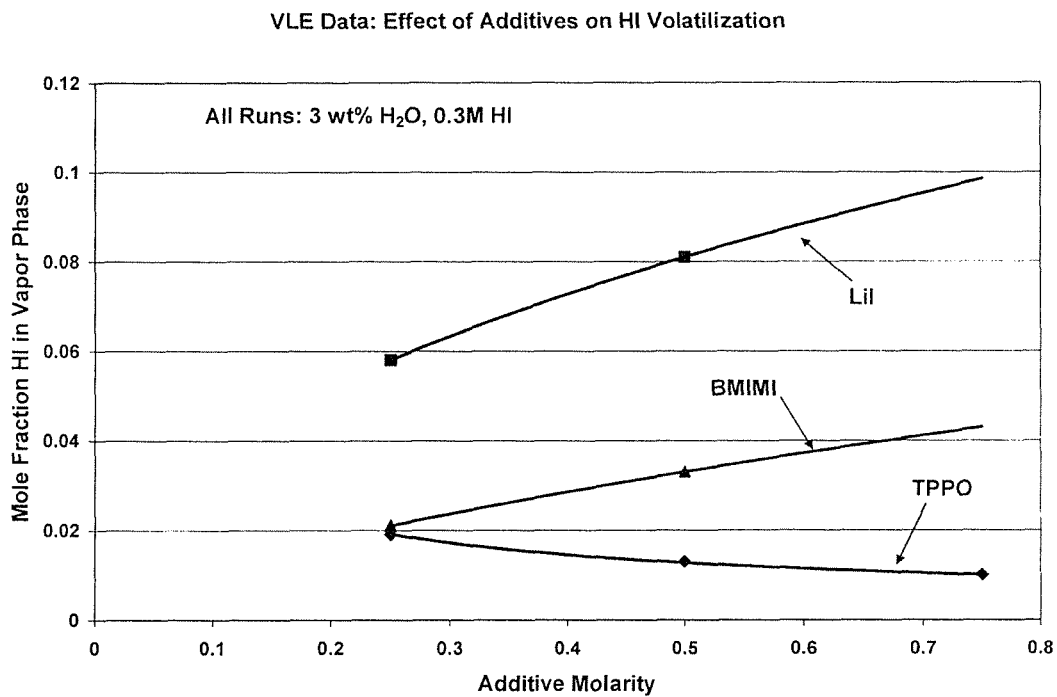
FIG. 13 depicts the results of investigations into the impact of triphenylphosphine oxide, lithium iodide, and 1-butyl, 3-methylimidazolium iodide on the VLE of hydrogen iodide in acetic acid comprising 3 wt. % of water.

FIGS. 12 and 13 show the effect of lithium iodide (LiI), triphenylphosphine oxide (TPPO), and 1-butyl, 4-methylimidazolium iodide (BMIMI) on the volatility of hydrogen iodide at a water concentration of 5.5-6 wt. % and 3 wt. %, respectively.

Those having ordinary skill in the art will appreciate that the illustrations in FIGS. 3 to 8 are vastly schematized and simplified to bring out the most pertinent aspects of the product flow. Accordingly, it will be readily apparent to those of ordinary skill that the lines which are represented in the figures may be embodied by pipes optionally comprising further process equipment such as valves, pumps, cooling or heating means, as well as additional reaction or separating zones. Also, although FIGS. 3 to 8 indicate entry points for feeds (→|) and points at which streams are withdrawn from a zone (|→), as well as relative positions of such feed and withdrawal points, those skilled in the art will readily appreciate that the positions and relations of those points are merely exemplary. For example, referring to FIG. 3, one having ordinary skill will readily appreciate that the feed of the vapor stream ($B_V$) through line (5) into the fractioning zone (4), may be located below the feed of the alkylimidazole into the fractioning zone (4) through line (11) thus providing that the vapor stream ($B_V$) flows counter current to the alkylimidazole stream when forming the mixture (C).

The following investigations and examples are intended to be illustrative only, and are not intended to be, nor should they be construed as, limiting the scope of the present invention in any way.

EXAMPLES

1. Vapor-Liquid-Equilibrium (VLE) Investigations

The investigations were carried out in two different types of recirculation apparatus as shown schematically in FIGS. 9 and 10. Apparatus 1 was used for the experiments described in Examples 1 to 3, the results of which are depicted in FIG. 11. Apparatus 2 was used for the experiments described in Examples 4 to 21 the results of which are compiled in Tables 2 and 3 and depicted in FIGS. 12 and 13.

General Procedure A:

In the case of Apparatus 1, a 1/flask was charged with a total of 500 grams of appropriate amounts of acetic acid, water, hydrogen iodide (HI) and optionally triphenylphosphine oxide (TPPO) or lithium iodide (LiI). The stirred solution was brought to reflux. After one hour of condensation/liquid return, a 10-20 gram sample of vapor condensate was collected. A 0.2 ml sample was also removed from the flask for analysis. A volume of acetic acid equivalent to the volume of the removed condensate sample was added to the flask and the solution was allowed to reflux for about 30 minutes before the sampling procedure was repeated and a further aliquot of acetic acid was added. This procedure was repeated until the concentration of water in the flask had decreased to the desired level.

General Procedure B:

In the case of Apparatus 2, the 150 grams of a mixture of appropriate amounts of acetic acid, water, hydrogen iodide (HI), lithium iodide (LiI), triphenylphosphine oxide (TPPO), 1-butyl, 4-methylimidazolium iodide (BMIMI), 1-butyl, 2,3-dimethylimidazo hum iodide (BDMIMI), and 1-dodecycl, 3-methylimidazolium iodide (DOMIMI) were charged to the flask under atmospheric pressure and slight $N_2$ purge. The mixture was refluxed for about 1 hour during which period the condensate was recirculated to the flask. Thereafter, a sample of the condensate and a sample of the mixture were withdrawn for analysis, and the experiment was terminated.

Water concentration in condensed vapor samples and in pot liquid samples was measured by Karl Fischer titration. Iodide concentration in those experiments containing iodide was determined either by titration with silver nitrate or by a visible spectrophotometric method in which iodide is first rapidly oxidized to iodine by hydrogen peroxide and then quantified by the iodine absorption band at 475 nm.

Validation of VLE Apparatus 1 and VLE Apparatus 2:

As those skilled in the art will appreciate, it is critical that the apparatus operate in adiabatic fashion in which only one equilibrium stage is present and in which there is no enrichment of the vapor in the more volatile component by partial condensation. As such, the suitability of Apparatus 1 and Apparatus 2 was validated before use by determining the water concentration in the vapor condensate at flask water concentrations of 5, 10 and 20 wt. % in acetic acid. The extent of enrichment of the more volatile water in the vapor phase upon heating the samples to reflux and upon analyzing a condensed vapor sample and a liquid pot sample, matched well with previous literature values as shown in Table 1 where all values are expressed as mole fractions.

TABLE 1

Validation of VLE Apparatus 1 and VLE Apparatus 2 by comparison with prior art data

| $H_2O$, Liq | $H_2O^1$, Vap | $H_2O^2$, Vap | $H_2O^3$, Vap | $H_2O^4$, Vap |
|---|---|---|---|---|
| 0.15 | 0.26 | 0.23 | 0.26 | 0.23 |
| 0.28 | 0.41 | 0.41 | 0.41 | 0.4 |
| 0.47 | 0.61 | 0.6 | 0.61 | |

[1] = Apparatus 1
[2] = Apparatus 2
[3] = EP 0 506 240
[4] = Brown et al., Aust. J. Sci. Res. Series A 3, 306 (1950)

Example 1

General Procedure A 500 grams of a solution composed of 12 wt. % water, 3.8 wt. % hydrogen iodide and 84.2 wt. % acetic acid was charged to the Apparatus 1 flask. As described above, the water concentration in the flask was decreased from 12 wt. % to about 5 wt. % in increments of about 0.5 wt. % by removal of aliquots of condensed vapor sample and replenishing the flask with a similar volume of acetic acid. The water and iodide concentration of the condensed vapor sample and of the pot solution were determined after each removal, thus allowing the mole fractions of all components to be calculated. The results are depicted in FIG. 11 which shows a rapid increase in hydrogen iodide in the vapor phase as water concentration in the pot is lowered.

Example 2

500 grams of a solution composed of 12 wt. % water, 3.8 wt. % hydrogen iodide, 13.0 wt. % triphenylphosphine oxide and 71.2 wt. % acetic acid was charged to Apparatus 1 and an experiment conducted as described in Example 1. The results are depicted in FIG. 11 which shows that in the presence of triphenylphosphine oxide, there is very little hydrogen iodide in the vapor phase compared to Example 1.

Example 3

500 grams of a solution composed of 12 wt. % water, 3.8 wt. % hydrogen iodide, 13.0 wt. % lithium iodide and 71.2 wt. % acetic acid was charged to Apparatus 1 and an experiment conducted as described in Example 1. The results are depicted in FIG. 11 which shows that in the presence of lithium iodide, there is a rapid increase in hydrogen iodide in the vapor phase, even when there remains a high mole fraction of water in the liquid phase.

Example 4

General Procedure B 150 grams of a solution composed of 5.8 wt. % water, 3.7 wt. % hydrogen iodide and 90.5 wt. % acetic acid was charged to the Apparatus 2 flask. After one hour of refluxing, a condensed vapor sample and a pot sample were removed for analysis. The results are compiled in Table 2 and depicted in FIG. 12.

Example 5

Example 4 was repeated with an initial solution composed of 5.8 wt. % water, 3.7 wt. % hydrogen iodide, 6.7 wt. % 1-butyl, 4-methylimidazolium iodide and 83.8 wt. % acetic acid. The results are compiled in Table 2 and depicted in FIG. 12.

Example 6

Example 4 was repeated with an initial solution composed of 5.8 wt. % water, 3.7 wt. % hydrogen iodide, 13.3 wt. % 1-butyl, 4-methylimidazolium iodide and 77.2 wt. % acetic acid. The results are compiled in Table 2 and depicted in FIG. 12.

Example 7

Example 4 was repeated with an initial solution composed of 6.0 wt. % water, 3.7 wt. % hydrogen iodide, 6.7 wt. % triphenylphosphine oxide and 83.6 wt. % acetic acid. The results are compiled in Table 2 and depicted in FIG. 12.

Example 8

Example 4 was repeated with an initial solution composed of 6.0 wt. % water, 3.7 wt. % hydrogen iodide, 13.3 wt. % triphenylphosphine oxide and 77.0 wt. % acetic acid. The results are compiled in Table 2 and depicted in FIG. 12.

Example 9

Example 4 was repeated with an initial solution composed of 6.0 wt. % water, 3.9 wt. % hydrogen iodide, 3.3 wt. % lithium iodide and 86.8 wt. % acetic acid. The results are compiled in Table 2 and depicted in FIG. 12.

Example 10

Example 4 was repeated with an initial solution composed of 5.5 wt. % water, 3.8 wt. % hydrogen iodide, 6.6 wt. % lithium iodide and 84.1 wt. % acetic acid. The results are compiled in Table 2 and depicted in FIG. 12.

TABLE 2

Effect of lithium iodide (LiI), triphenylphosphine oxide (TPPO), and 1-butyl, 4-methylimidazolium iodide (BMIMI) on volatilization of hydrogen iodide (HI) from acetic acid containing 5.5-6 wt. % of water

| Ex. | Additive | Additive Concentration [M] | Mol Fraction of HI in Condensed Vapor |
|---|---|---|---|
| 04 | None (control) | —/— | 0.012 |
| 05 | BMIMI | 0.25 | 0.01 |
| 06 | | 0.5 | 0.009 |
| 07 | TPPO | 0.25 | 0.009 |
| 08 | | 0.5 | 0.007 |
| 09 | LiI | 0.25 | 0.015 |
| 10 | | 0.5 | 0.058 |

Example 11

Example 4 was repeated with an initial solution composed of 2.9 wt. % water, 3.7 wt. % hydrogen iodide and 93.4 wt. % acetic acid. The results are compiled in Table 3 and depicted in FIG. 13.

Example 12

Example 4 was repeated with an initial solution composed of 2.9 wt. % water, 3.7 wt. % hydrogen iodide, 6.7 wt. % 1-butyl, 4-methylimidazolium iodide and 86.7 wt. % acetic acid. The results are compiled in Table 3 and depicted in FIG. 13.

Example 13

Example 4 was repeated with an initial solution composed of 2.9 wt. % water, 3.7 wt. % hydrogen iodide, 13.3 wt. % 1-butyl, 4-methylimidazolium iodide and 80.1 wt. % acetic acid. The results are compiled in Table 3 and depicted in FIG. 13.

Example 14

Example 4 was repeated with an initial solution composed of 2.9 wt. % water, 3.7 wt. % hydrogen iodide, 7.0 wt. % 1-butyl, 2,3-dimethylimidazolium iodide and 86.4 wt. % acetic acid. The results are compiled in Table 3 and depicted in FIG. 13.

Example 15

Example 4 was repeated with an initial solution composed of 2.9 wt. % water, 3.7 wt. % hydrogen iodide, 9.5 wt. % 1-dodecycl, 3-methylimidazolium iodide and 83.9 wt. % acetic acid. The results are compiled in Table 3 and depicted in FIG. 13.

Example 16

Example 4 was repeated with an initial solution composed of 2.9 wt. % water, 3.7 wt. % hydrogen iodide, 6.7 wt. % triphenylphosphine oxide, 6.7 wt. % 1-butyl, 4-methylimidazolium iodide and 80.0 wt. % acetic acid. The results are compiled in Table 3 and depicted in FIG. 13.

Example 17

Example 4 was repeated with an initial solution composed of 2.9 wt. % water, 3.7 wt. % hydrogen iodide, 6.7 wt. % 1-butyl, 4-methylimidazolium iodide, 3.3 wt. % lithium iodide and 83.4 wt. % acetic acid. The results are compiled in Table 3 and depicted in FIG. 13.

Example 18

Example 4 was repeated with an initial solution composed of 3.1 wt. % water, 3.9 wt. % hydrogen iodide, 6.6 wt. % triphenylphosphine oxide and 86.4 wt. % acetic acid. The results are compiled in Table 3 and depicted in FIG. 13.

Example 19

Example 4 was repeated with an initial solution composed of 2.9 wt. % water, 3.7 wt. % hydrogen iodide, 13.3 wt. % triphenylphosphine oxide and 80.1 wt. % acetic acid. The results are compiled in Table 3 and depicted in FIG. 13.

Example 20

Example 4 was repeated with an initial solution composed of 2.9 wt. % water, 3.7 wt. % hydrogen iodide, 3.3 wt. % lithium iodide and 90.1 wt. % acetic acid. The results are compiled in Table 3 and depicted in FIG. 13.

Example 21

Example 4 was repeated with an initial solution composed of 2.9 wt. % water, 3.7 wt. % hydrogen iodide, 6.6 wt. % lithium iodide and 86.8 wt. % acetic acid. The results are compiled in Table 3 and depicted in FIG. 13.

TABLE 3

Effect of lithium iodide (LiI), triphenylphosphine oxide (TPPO), 1-butyl, 4-methylimidazolium iodide (BMIMI), 1-butyl, 2,3-dimethylimidazolium iodide (BDMIMI), and 1-dodecycl, 3-methylimidazolium iodide (DOMIMI) on volatilization of hydrogen iodide (HI) from acetic acid containing 3 wt. % of water

| Ex. | Additive | Additive Concentration [M] | Mol Fraction of HI in Condensed Vapor |
|---|---|---|---|
| 11 | None (control) | —/— | 0.048 |
| 12 | BMIMI | 0.25 | 0.021 |
| 13 | | 0.5 | 0.033 |
| 14 | BDMIMI | 0.25 | 0.023 |
| 15 | DOMIMI | 0.25 | 0.041 |
| 16 | TPPO + BMIMI | 0.25 + 0.25 | 0.017 |
| 17 | LiI + BMIMI | 0.25 + 0.25 | 0.049 |
| 18 | TPPO | 0.25 | 0.019 |
| 19 | | 0.5 | 0.013 |
| 20 | LiI | 0.25 | 0.058 |
| 21 | | 0.5 | 0.081 |

In particular, Table 2 and FIG. 12 illustrate that the effect of the iodide salt (BMIMI) on the suppression of hydrogen iodide is similar to that of triphenylphosphine oxide (TPPO). In contrast, lithium iodide increases the volatility of hydrogen iodide in a concentration dependent manner, i.e., an increase of almost an order of magnitude is observed when the concentration of lithium iodide is increased from 0.25 M to 1.0 M.

We claim:
1. A process for producing acetic acid which comprises:
    (a) carbonylating methanol in the presence of a catalyst in a reaction zone to obtain a reaction mixture (A) comprising acetic acid, hydrogen iodide, methyl iodide, water and the catalyst;
    (b) separating at least a part of the reaction mixture (A) in a flash zone to obtain a liquid stream ($B_L$) comprising the catalyst, and a vapor stream ($B_V$) comprising acetic acid, hydrogen iodide, methyl iodide and water, and withdrawing the vapor stream ($B_V$) from the flash zone;
    (c) reacting the withdrawn vapor stream ($B_V$) with at least one alkylimidazole to obtain a composition (C); and
    (d) separating the acetic acid from the composition (C).
2. The process of claim 1, wherein step (d) comprises
    ($d_1$) fractioning the composition (C) in a fractioning zone to obtain a product stream ($D_P$) comprising the acetic acid and a liquid stream ($D_L$) comprising water and at least one iodide salt formed by reacting the alkylimidazole with hydrogen iodide or with methyl iodide.
3. The process of claim 2, wherein the vapor stream ($B_V$) and the at least one alkylimidazole are reacted in the fractioning zone.
4. The process of claim 2, wherein the liquid stream ($D_L$) is recycled to the reaction zone.
5. The process of claim 4, wherein the liquid stream ($D_L$) is recycled to the reaction zone by firstly introducing ($D_L$) into the flash zone to obtain a combination of the liquid streams

($D_L$) and ($B_L$), and subsequently recycling at least a part of the combination of ($D_L$) and ($B_L$) to the reaction zone.

6. The process of claim 4, wherein the at least one alkylimidazole is employed in step (c) in an amount sufficient to establish a steady state concentration of from about 2 to about 20% by weight of the iodide salt in the reaction mixture (A).

7. The process of claim 1, wherein the alkylimidazole is a compound of formula (I)

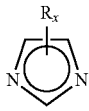

wherein x is 1, 2 or 3, and each R independently is $C_1$-$C_6$-alkyl.

8. The process of claim 7, wherein the alkylimidazole is a compound of formula (Ia)

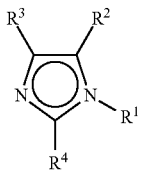

wherein $R^1$ is hydrogen, or $C_1$-$C_6$-alkyl;

$R^2$, $R^3$, $R^4$ each independently, is hydrogen, or $C_1$-$C_2$-alkyl;

and wherein at least one of $R^1$, $R^2$, $R^3$ and $R^4$ is different from hydrogen, and at least one of $R^1$, $R^2$, $R^3$ and $R^4$ is hydrogen.

9. The process of claim 7, wherein the alkylimidazole is 1-methylimidazole, 1-ethylimidazole, 1-propylimidazole, 1-isopropylimidazole, 1-(1-butyl)imidazole, 1-(2-butyl)imidazole, 1-isobutylimidazole, 1-tert-butylimidazole, 3-methylimidazole, 3-ethylimidazole, 4-methylimidazole, 4-ethylimidazole, 1,4-dimethylimidazole, 1,4-diethylimidazole, 1-ethyl-4-methylimidazole, 4-ethyl-1-methylimidazole, 2-methyl-1-propylimidazole, 4-methyl-1-propylimidazole, 5-methyl-1-propylimidazole, 2,4-dimethyl-1-propylimidazole, 2,5-dimethyl-1-propylimidazole, 1-isopropyl-2-methylimidazole, 1-isopropyl-4-methylimidazole, 1-isopropyl-5-methylimidazole, 2,4-dimethyl-1-isopropylimidazole, 2,5-dimethyl-1-isopropylimidazole, 1-(1-butyl)-2-methylimidazole, 1-(1-butyl)-4-methylimidazole, 1-(1-butyl)-5-methylimidazole, 1-(1-butyl)-2,4-dimethylimidazole, 1-(1-butyl)-2,5-dimethylimidazole, 1-(2-butyl)-2-methylimidazole, 1-(2-butyl)-4-methylimidazole, 1-(2-butyl)-5-methylimidazole, 1-(2-butyl)-2,4-dimethylimidazole, 1-(2-butyl)-2,5-dimethylimidazole, 1-isobutyl-2-methylimidazole, 1-isobutyl-4-methylimidazole, 1-isobutyl-5-methylimidazole, 2,4-dimethyl-1-isobutylimidazole, 2,5-dimethyl-1-isobutylimidazole, 1-tert-butyl-2-methylimidazole, 1-tert-butyl-4-methylimidazole, 1-tert-butyl-5-methylimidazole, 1-tert-butyl-2,4-dimethylimidazole, or 1-tert-butyl-2,5-dimethylimidazole.

10. The process of claim 1, wherein the catalyst is a rhodium catalyst.

11. The process of claim 1, wherein the reaction mixture (A) comprises at least one catalyst stabilizer selected from the group consisting of phosphine oxides and iodides of a metal of Group 1 and 2 of the Periodic Table of the Elements.

12. The process of claim 11, wherein the stabilizer is triphenylphosphine oxide and/or lithium iodide.

13. The process of claim 1, wherein the reaction mixture (A) does not comprise a catalyst stabilizer selected from the group consisting of phosphine oxides and iodides of metals of Group 1 and 2 of the Periodic Table of the Elements.

14. The process of claim 1, wherein the reaction mixture (A) comprises water in a concentration of from about 2% to about 10% by weight.

\* \* \* \* \*